United States Patent
Resendez et al.

(10) Patent No.: US 11,892,401 B2
(45) Date of Patent: Feb. 6, 2024

(54) BORONIC ACID APPENDED NAPHTHYL-PYRIDINIUM FLUORESCENT SACCHARIDE SENSORS FOR EARLY DETECTION OF GASTROINTESTINAL DISEASES

(71) Applicant: The Board of Trustees of the Leland Stanford Junior University, Stanford, CA (US)

(72) Inventors: Angel Resendez, Palo Alto, CA (US); Sanjay Malhotra, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 860 days.

(21) Appl. No.: 16/966,808

(22) PCT Filed: Feb. 12, 2019

(86) PCT No.: PCT/US2019/017635
§ 371 (c)(1),
(2) Date: Jul. 31, 2020

(87) PCT Pub. No.: WO2019/160854
PCT Pub. Date: Aug. 22, 2019

(65) Prior Publication Data
US 2021/0364437 A1 Nov. 25, 2021

Related U.S. Application Data

(60) Provisional application No. 62/630,034, filed on Feb. 13, 2018.

(51) Int. Cl.
G01N 21/64 (2006.01)
C07F 5/02 (2006.01)
A61B 5/00 (2006.01)

(52) U.S. Cl.
CPC ......... *G01N 21/6428* (2013.01); *C07F 5/025* (2013.01); *A61B 5/0071* (2013.01); *A61B 5/4255* (2013.01)

(58) Field of Classification Search
None
See application file for complete search history.

(56) References Cited

U.S. PATENT DOCUMENTS

| 6,673,625 | B2 | 1/2004 | Satcher et al. |
| 8,979,790 | B2 | 3/2015 | Markle et al. |
| 11,255,860 | B2 * | 2/2022 | Crane ............... A61B 5/1473 |

(Continued)

*Primary Examiner* — Edwin C Gunberg
(74) *Attorney, Agent, or Firm* — Pamela J. Sherwood; Bozicevic, Field & Francis LLP

(57) ABSTRACT

The present disclosure relates to novel boronic acid receptor compounds and their use in methods of quantifying a saccharide appearing in a sample. Provided are methods of measuring the concentration of a saccharide in a sample as well as methods of measuring the concentration of a halogenated saccharide in a sample. In certain aspects the sample is a biological sample and the methods further include correlating the measured concentration of saccharide in the biological sample to the gastrointestinal permeability in the individual. Disclosed are also kits for performing the above methods.

19 Claims, 10 Drawing Sheets

(56) References Cited

U.S. PATENT DOCUMENTS

| | | | |
|---|---|---|---|
| 2002/0043651 A1* | 4/2002 | Darrow | G01N 33/582 |
| | | | 252/408.1 |
| 2008/0305009 A1 | 12/2008 | Gamsey et al. | |
| 2009/0149656 A1 | 6/2009 | Singaram et al. | |
| 2012/0009126 A1* | 1/2012 | Singaram | G01N 33/542 |
| | | | 424/9.1 |
| 2017/0285038 A1* | 10/2017 | Singaram | G01N 21/6428 |

* cited by examiner

US 11,892,401 B2

BORONIC ACID APPENDED NAPHTHYL-PYRIDINIUM FLUORESCENT SACCHARIDE SENSORS FOR EARLY DETECTION OF GASTROINTESTINAL DISEASES

CROSS REFERENCE

This application claims the benefit and is a 371 application of PCT Application No. PCT/US2019/017635, filed Feb. 12, 2019, which claims benefit of U.S. Provisional Patent Application No. 62/630,034, filed Feb. 13, 2018, which applications are incorporated herein by reference in their entirety.

GOVERNMENT RIGHTS

This invention was made with Government support under contract TR001085 awarded by the National Institutes of Health. The Government has certain rights in the invention.

BACKGROUND

The small intestine has the dual function of being an absorptive organ as well as a barrier to permeation of toxic compounds and macromolecules. Systemic problems result if either of these functions are disrupted. Increased permeability of the intestinal mucosal barrier correlates with a number of frequently seen clinical disorders, while decreased permeability appears as a fundamental cause of malnutrition, malabsorption, and failure to thrive. Changes in gut permeability is seen in disorders such as inflammatory bowel disease, Crohn's disease, inflammatory joint disease, food allergy, celiac disease, Rheumatoid arthritis, Ankylosing spondylitis, Reiter's syndrome, chronic dermatological conditions, schizophrenia, irritable bowel syndrome, allergic disorders, type 1 and type 2 diabetes mellitus, obesity, cancer, environmental enteropathy, autism spectrum disorders, Parkinson's disease, chemotherapy monitoring and drug safety.

Current assessment of small intestinal permeability involves the oral ingestion of sugar markers, lactulose and mannitol, followed by collection of urine for 6 hours. The amount of lactulose and mannitol in the urine is measured using two different HPLC configurations (e.g., ion exchange and reverse phase), coupled to detectors such as Mass Spectrometers. Alternatively, NADPH-coupled enzyme assays are used. Both of these detection techniques require considerable time and cost. Currently available technology does not allow rapid, direct quantification of the sugar markers because neither lactulose nor mannitol has intrinsic absorbance or fluorescence.

Thus, a need exists to simplify the measurement and increase throughput of intestinal permeability while lowering the cost per sample.

SUMMARY

The present disclosure relates to novel boronic acid receptor compounds and their use in methods of quantifying a saccharide appearing in a sample. Provided are methods of measuring the concentration of a saccharide in a sample as well as methods of measuring the concentration of a halogenated saccharide in a sample. In certain aspects the sample is a biological sample and the methods further include correlating the measured concentration of saccharide in the biological sample to the gastrointestinal permeability in the individual. In certain aspects the boronic acid receptor is used as a standalone probe for measuring the concentration of a saccharide in a sample (i.e. a one-component system). In certain other aspects, the boronic acid receptors are coupled to a fluorophore (e.g. an anionic dye) for measuring the concentration of a saccharide in a sample (i.e. a two-component system). Disclosed are also kits for performing the above methods.

BRIEF DESCRIPTION OF THE FIGURES

The invention is best understood from the following detailed description when read in conjunction with the accompanying figures. It is emphasized that, according to common practice, the various features of the figures are not to-scale. On the contrary, the dimensions of the various features are arbitrarily expanded or reduced for clarity. Included in the drawings are the following figures. It is understood that the figures, described below, are for illustration purposes only. The figures are not intended to limit the scope of the present teachings in any way.

FIG. 2, panel B illustrates the proposed mechanism of signal transduction for a two-component fluorescent probe based on a subject boronic acid receptor and HPTS.

FIG. 6, panel A: HPTS-(1); FIG. 6, panel B: HPTS-(3); FIG. 6, panel C: HPTS-(4); FIG. 6, panel D: TSPP-(1); FIG. 6, panel E: TSPP-(3); and FIG. 6, panel F: TSPP-(4). Each fluorescence recovery measurements were carried out in 0.1 M sodium phosphate buffer pH 7.4 and each dye was 4 μM.

DEFINITIONS

Figure 1:
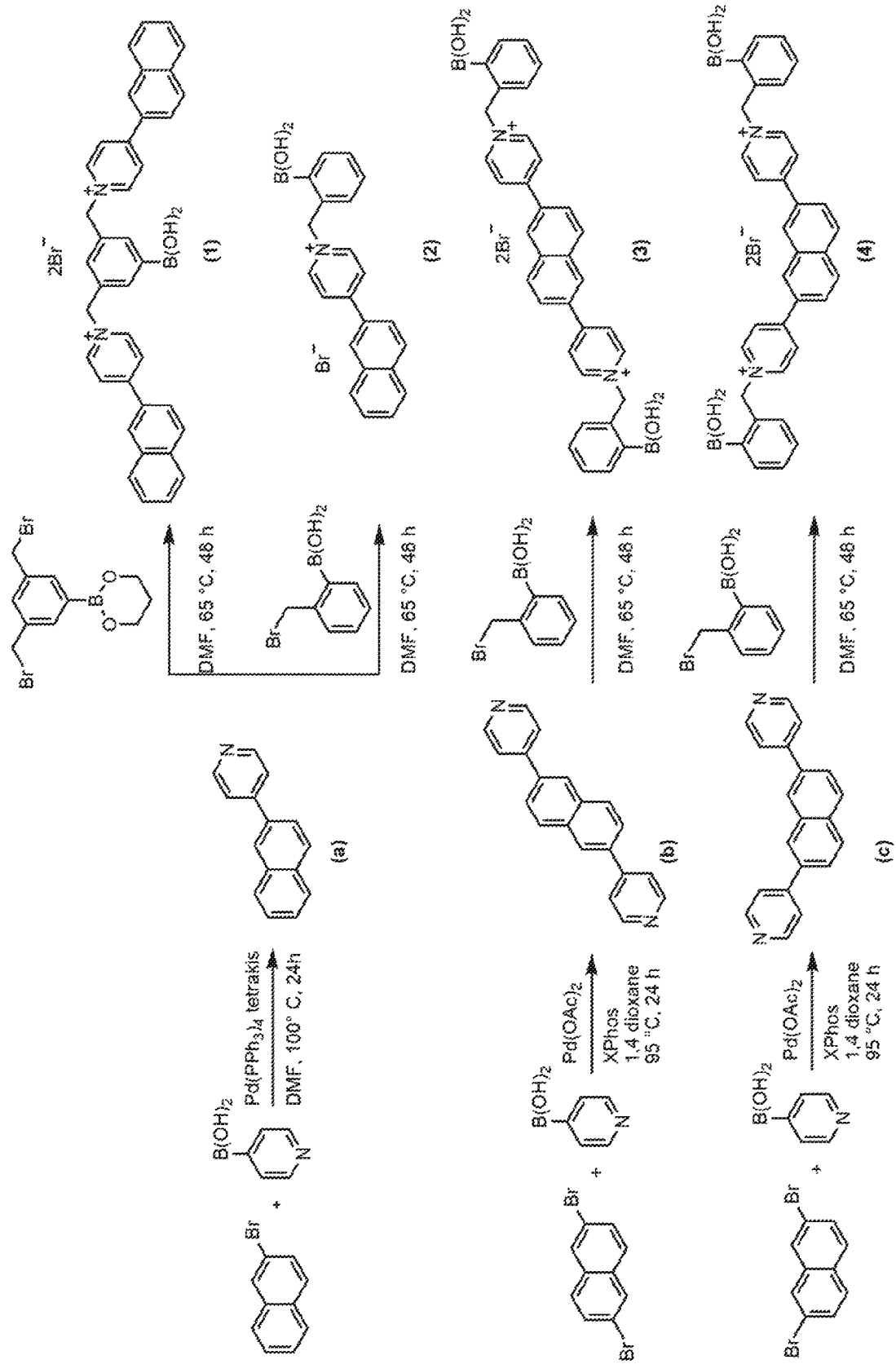
FIG. 1 illustrates the synthesis of exemplary boronic acid receptor compounds (1-4).

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

The terminology used herein is for the purpose of describing particular embodiments only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within one or more than one standard deviation, per the practice in the art. Alternatively, "about" can mean a range of up to 20%, of a given value. Where particular values are described in the application and claims, unless otherwise stated the term "about" meaning within an acceptable error range for the particular value should be assumed.

Unless otherwise defined, all technical and scientific terms used herein have the same meaning as commonly understood by one of ordinary skill in the art to which this invention belongs.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless otherwise stated, the following terms used in this application, including the specification and claims, have definitions given below.

The term "saccharide" or "sugar" may be used interchangeably and as used herein contemplates a short chain, water-soluble carbohydrate. Saccharide may be a monosaccharide, a disaccharide, or an oligosaccharide. The saccharide may be naturally occurring or synthetically prepared in the laboratory. In some embodiments the saccharide is digestible, while in other embodiments the saccharide is non-digestible. The term "saccharide" or "sugar" also includes sugar alcohols. As used herein, the term "sugar alcohol" is defined as a polyhydric alcohol (also known as a polyol) formed by the reduction of the carbonyl group of a sugar to a hydroxyl group, with no more than one hydroxy group being attached to any one carbon atom of the sugar alcohol. Examples of sugar alcohols include, but are not limited to, mannitol, sorbitol and xylitol.

The terms "subject" or "individual" as used herein, refers to an animal, preferably a mammal, most preferably a human, who is in the need of assessment of intestinal permeability. In some embodiments, the intestinal permeability may be small intestinal permeability. In some embodiments, the terms subject or individual are used interchangeably with the term patient.

The term "biological sample" as used herein, refers to a sample obtained from an individual. The term "biological fluid" as used herein contemplates a liquid biological sample with biomolecules, bioparticles, blood, sweat, saliva, amniotic fluid, lacrimal fluid, urine, milk, mucus, pus, semen, cerebrospinal fluid, vaginal fluid, and combinations thereof. Examples of biomolecules are, but not limited to, nucleic acids, peptides, and enzymes. Examples of bioparticles are, but not limited to, cells, organelles etc.

The term "organoboron" or "organoboronic" or "organoborane" as used herein refers to boron containing organic compounds that possess one or more alkyl, aryl, heteroalkyl, or heretoaryl substituents. The term "boronic acid" contemplates boron containing organic compounds that possess one alkyl, aryl, heteroalkyl, or heretoaryl substituent, and two hydroxyl groups. The term "borinic acid" contemplates boron containing organic compounds that possess two alkyl, aryl, heteroalkyl, or heteroaryl substituents, and one hydroxyl group.

The term HPTS refers to 8-hydroxypyrene, 1,3,6-trisulfonic acid trisodium salt.

The term TSPP refers to tetrakis (4-sulfophenyl) porphine.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —OR, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOW, —SO$_2$R, —SO$_3$R, —S(O)$_2$N(R$^N$)$_2$, phosphate, phosphonate, cycloalkyl, cycloalkenyl, aryl and heteroaryl, where R$^N$ is a substituent bonded to a nitrogen.

The terms "aryl," "aromatic group" or "aromatic ring" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —B(OH)$_2$, —B(R)$_2$—CN, —NO$_2$, —CO$_2$R, —C(O)R, —OR, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "heteroalkyl" as used herein contemplates an alkyl with one or more heteroatoms.

The term "heteroatom" refers to N, O and S.

The term "aralkyl" refers to an alkyl group with an aryl substituent, and the term "alkaryl" refers to an aryl group with an alkyl substituent, wherein "alkyl" and "aryl" are as defined above.

The term "heteroaryl" contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of halo, alkyl, —B(OH)$_2$, —B(R)$_2$, —CN, —NO$_2$, —CO$_2$R, —C(O)R, —OR, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

By "substituted" as in "substituted aryl," "substituted heteroaryl," "substituted heteroaryl cation," and the like, as alluded to in some of the aforementioned definitions, is meant that in the aryl, heteroaryl or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated, e.g. a boronic acid group. Unless otherwise indicated, any of the groups described herein are to be interpreted as including substituted and/or heteroatom-containing moieties, in addition to unsubstituted groups.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "cation" refers to any molecule, portion of a molecule (e.g., Zwitterion), cluster of molecules, molecular complex, moiety, or atom, that contains a net positive charge or that can be made to contain a net positive charge. In certain embodiments, the "heteroaryl" is a "heteroaryl cation" e.g. pyridinium.

The term "anion" refers to any molecule, portion of a molecule (e.g., Zwitterion), cluster of molecules, molecular complex, moiety, or atom that contains a net negative charge or that can be made to contain a net negative charge.

The term "fluorophore" as used herein contemplates a fluorescent chemical compound that can re-emit light upon light excitation. Examples of fluorophore include, but are not limited to, 8-Hydroxy-1,3,6-pyrenetrisulfonic acid (HPTS) and 8-methoxypyrene-1,3,6-trisulfonic acid (MPTS). In one embodiment, fluorophore refers to HPTS. In another embodiment, fluorophore refers to TSPP.

The terms "4× premix buffer," "4× premix," "4× buffer," or "4×" as used herein contemplates a buffer comprising 100 mM 4-(2-Hydroxyethyl)piperazine-1-ethanesulfonic acid (HEPES), 100 mM sodium phosphate and 0.04% w/v Triton X-100 (or alternatively, polyethylene glycol sorbitan monolaurate) at pH 7.4.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112. In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

DETAILED DESCRIPTION OF THE EMBODIMENTS

As summarized above, aspects of the present disclosure include boronic acid receptors, and methods for quantifying a saccharide in a sample. Aspects of the methods include measuring the concentration of a saccharide in a sample and measuring the concentration of a halogenated saccharide in a sample. In certain aspects the sample is a biological sample and the methods further include correlating the measured concentration of saccharide in the biological sample to the gastrointestinal permeability in the individual. In certain aspects the boronic acid receptor is used as a standalone probe for measuring the concentration of a saccharide in a sample (i.e. a one-component system). In certain other aspects, the boronic acid receptors are coupled to a fluorophore (e.g. an anionic dye) for measuring the concentration of a saccharide in a sample (i.e. a two-component system). Also provided are kits for performing the subject methods. These boronic acid receptors and methods find use in a variety of applications in which the detection and quantification of a saccharide is desired, for example, assessing for a condition that is associated with increased gastrointestinal (GI) permeability.

Compounds

As summarized above, aspects of the disclosure include boronic acid receptor compounds. In some cases, the compounds include naphthyl-pyridinium core structures. Exemplary compounds including naphthyl-pyridinium core structures are set forth in the following structures (1)-(11) and formulae (I)-(IB).

Boronic acids are known to undergo reversible covalent interactions with hydroxyl functional groups, which are commonly found in saccharides. Since saccharides have multiple hydroxyl groups, it has not been fully elucidated how boronic acid receptors bind to their saccharide targets and it is not well understood what exact position on the saccharides the boronic acid reacts. What is understood is that boronic acids form covalent bonds with the hydroxyl groups in the cis 1,2 or 1,3 positions to form five or six membered rings. This does not always hold true: if this were the case, then every boronic acid receptor made should follow a similar pattern for a range of saccharides with high selectivity and sensitivity. Most of the focus has been on developing sensitive and selective boronic acid receptors for glucose and fructose, although these are important saccharides, there are other saccharides that are not commonly studied and are becoming recognized as equally important. There has been a growing interest in using specific saccharides as biomarkers (lactulose, mannitol, sucralose, and sucrose) for assessing gastrointestinal permeability. Because each saccharide is structurally diverse, the sensitive boronic receptor that has been used for glucose or fructose does not suffice. Instead, presently disclosed is a new diverse library of boronic acid receptors that have unique structural and electronic properties, are stable and require minimal concentrations in the methods for saccharide detection disclosed herein. The subject boronic acid receptors may be used as standalone probes in methods for measuring the concentration of a saccharide in a sample (one-component systems), or may be coupled to a fluorophore (e.g. an anionic dye) in a two component system for measuring the concentration of a saccharide in a sample. In addition, the subject boronic acid receptors are readily synthesized in just 2 steps with good to excellent yields (see FIG. 1).

Based on using simple starting materials that require short syntheses to obtain the subject boronic acid receptors, the synthetic approach presented herein is advantageous in developing a practical system that can be utilized by clinicians. Overall, the synthetic strategy to the subject boronic acid receptors reduces molecular complexity, allows flexibility in multiple areas, and produces stable boronic acid receptors for developing a platform that can be used as a standalone probe or coupled to a fluorophore in a two component system for detecting and measuring the concentration of a saccharide in a sample. The presently disclosed boronic acid receptors are used in the inventors two component system and are capable of detecting the saccharide biomarker lactulose in minimal concentrations. Further, the presently disclosed boronic acid receptors are capable of detecting saccharides in the absence of any additional fluorophores. Inventors discovered that the subject boronic acid receptors may be used as standalone fluorescent probes, and exemplary receptor compounds exhibited at least a 2.5-fold increase in fluorescence intensity in physiological conditions which it is believed stems from the neutralization of the pyridinium nitrogen upon the saccharide diol recognition that in turn perturbs the chromophoric properties of the naphthalene core. The presently disclosed one and two component systems for the detection and quantification of saccharides relies on a boronic acid receptor that contains at least one cationic charge and at least one naphthalene substituent.

In some cases, the subject boronic acid receptor is of formula (I):

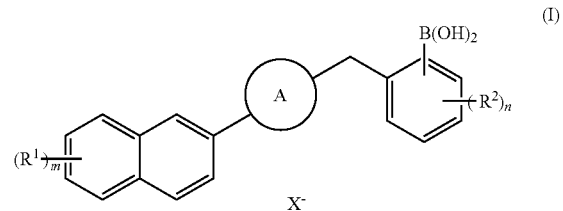

wherein

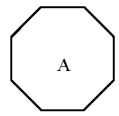

is selected from the group consisting of

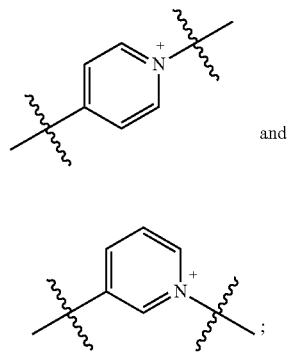

$R^1$ and $R^2$ are independently selected from an alkaryl group, a substituted alkaryl group, an aralkyl group, a substituted aralkyl group, aryl group (e.g. phenyl, naphthyl etc.), a substituted aryl group, a heteroaryl group, a substituted heteroaryl group (e.g., substituted with a boronic acid), a heteroaryl cation (e.g. pyridinium), a substituted heteroaryl cation, heterocycle group, a substituted heterocycle group;

n and m are independently an integer from 0 to 4; and $X^-$ is a counter ion, wherein the number of counter ions is equivalent to the number of cations in the receptor.

In one embodiment of a boronic acid receptor of formula (I), the group

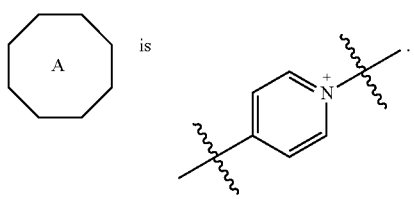

In another embodiment, the group

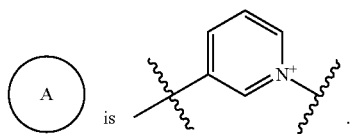

In certain cases of a boronic acid receptor, the formula (I) has the structure of formula (IA) or (IB):

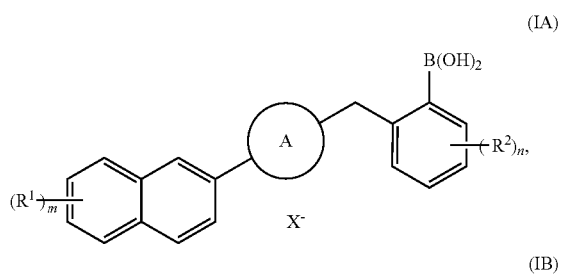

wherein:

is selected from the group consisting of,

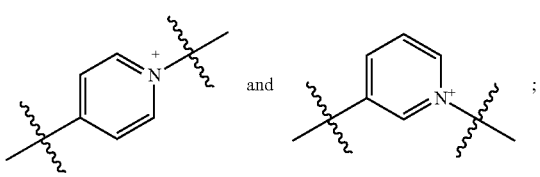

$R^1$ and $R^2$ are independently selected from an alkaryl group, a substituted alkaryl group, an aralkyl group, a substituted aralkyl group, aryl group (e.g. phenyl, naphthyl etc.), a substituted aryl group, a heteroaryl group, a substituted heteroaryl group (e.g., substituted with a boronic acid), a heteroaryl cation (e.g. pyridinium), a substituted heteroaryl cation, heterocycle group, a substituted heterocycle group;

n and m are independently an integer from 0 to 4; and $X^-$ is a counter ion, wherein the number of counter ions is equivalent to the number of cations in the receptor.

In one embodiment of a boronic acid receptor of formulas (I), (IA) or (IB), m is 0, n is 1 and $R^2$ is a substituted heteroaryl cation. In certain cases, m is 0, n is 2 and $R^2$ is a substituted heteroaryl cation. In certain cases, m is 0, n is 3 and $R^2$ is a substituted heteroaryl cation. In certain cases, in is 0, n is 4 and $R^2$ is a substituted heteroaryl cation. In some cases, the heteroaryl cation is a pyridinium group.

In one embodiment of a boronic acid receptor of formulas (I), (IA) or (IB), n is 0, m is 1 and $R^2$ is a substituted heteroaryl cation. In certain cases, n is 0, m is 2 and $R^2$ is a substituted heteroaryl cation. In certain cases, n is 0, m is 3 and $R^2$ is a substituted heteroaryl cation. In certain cases, n is 0, m is 4 and $R^2$ is a substituted heteroaryl cation.

In some embodiments of a boronic acid receptor of formulas (I), (IA) or (IB), $R^1$ or $R^2$ are independently selected from a substituted heteroaryl cation substituted with a group selected from, alkyl, boronic acid, aryl, alkyl aryl, an aryl substituted with a boronic acid group and any combination thereof. In some cases, the heteroaryl cation is a pyridinium group. In some cases, the pyridinium group is N-alkylated and further substituted with an aryl group. In certain instances the aryl group is a naphthyl group. In some cases, the aryl substituent is para to the N atom of the pyridinium group. In other cases, the pyridinium group is substituted at N with an alkaryl group. In some cases the alkaryl group may be further substituted on the aryl portion with a boronic acid group.

In certain instances of a boronic acid receptor of formulas (I), (IA) or (1B), $R^1$ and $R^2$ are independently selected from the group consisting of

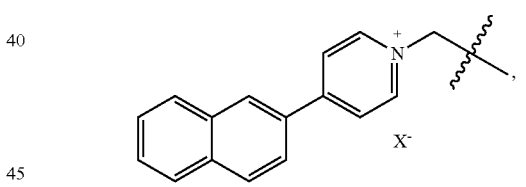

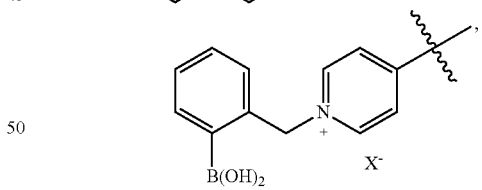

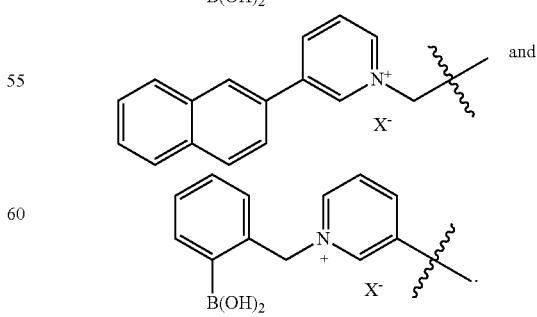

In certain cases of a boronic acid receptor of formulas (I), (IA) or (IB), the counter ion $X^-$ is a halogen. In some cases, X⁻ is chloride. In some cases, X⁻ is iodide. In certain cases X⁻ is fluoride. In certain other cases, X⁻ is bromide.

In certain cases of a boronic acid receptor of formulas (I), (IA) or (IB), the number of cations and counter ions are each 2. In other cases, the number of cations and counter ions are each 1. In other cases, the number of cations and counter ions are each 3. In certain other cases, the number of cations and counter ions are each 4.

In some embodiments of a boronic acid receptor the formulas (I), (IA) or (IB), have a structure selected from the group consisting of:

(1)
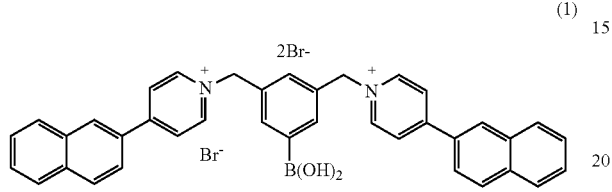

(2)
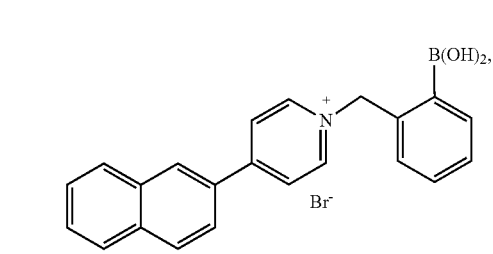

(3)
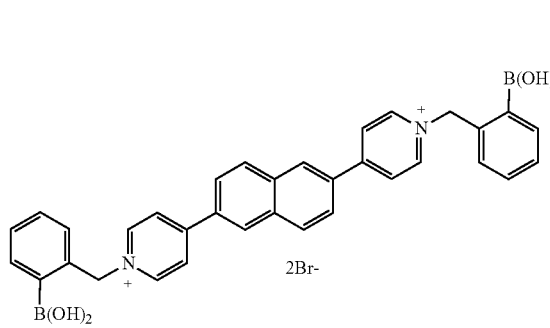

(4)
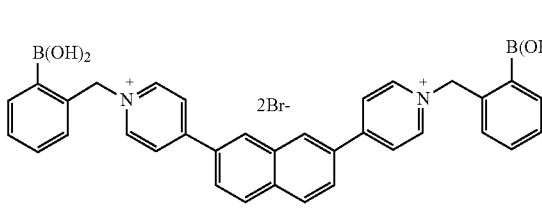

(5)
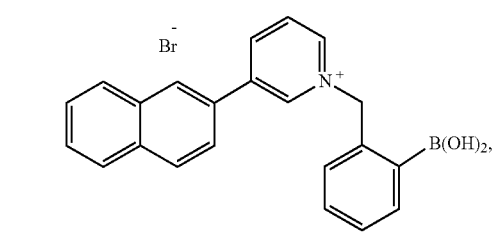

(6)
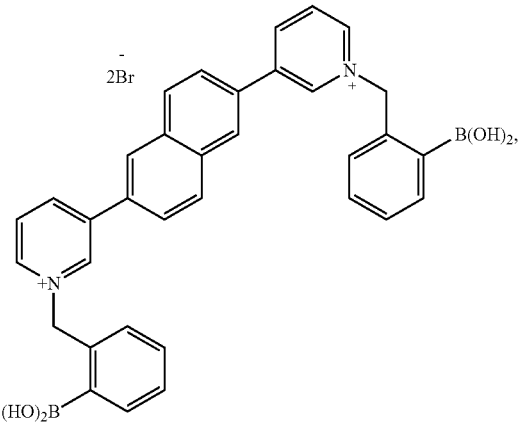

(7)
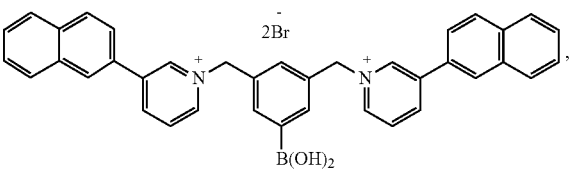

(8)
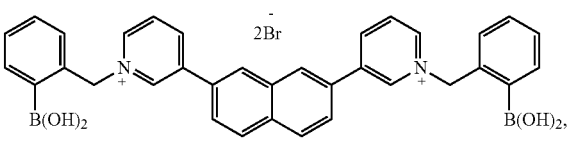

(9)
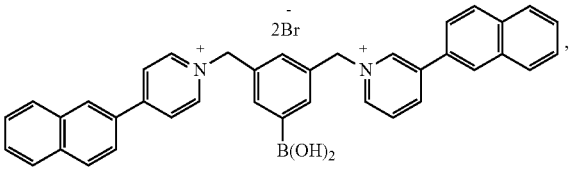

(10)
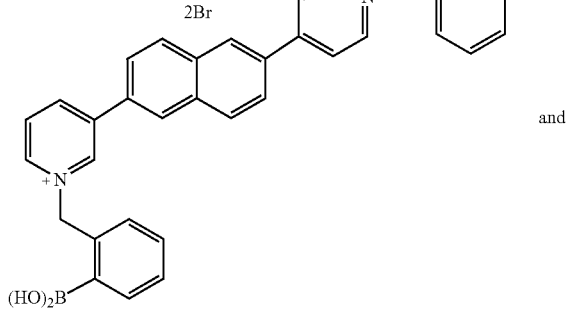

and (11)

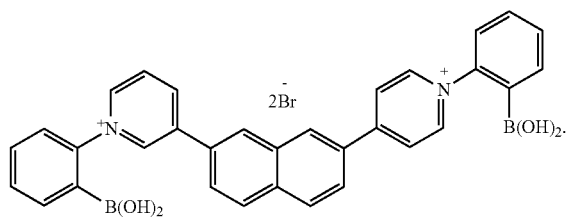

Methods

As summarized above, aspects of the present disclosure include methods of quantifying a saccharide in a sample using the subject boronic acid receptor compounds. Provided are methods of measuring the concentration of a saccharide in a sample as well as methods of measuring the concentration of a halogenated saccharide in a sample. In certain aspects the subject boronic acid receptor is used as a standalone probe for measuring the concentration of a saccharide in a sample (i.e. a one-component system). In certain other aspects, the subject boronic acid receptors are coupled to a fluorophore (e.g. an anionic dye) for measuring the concentration of a saccharide in a sample (i.e. a two-component system). In certain aspects of the methods, the first step involves modification of a halogenated saccharide to generate the corresponding hydroxyl saccharide derivative. In certain aspects the sample is a biological sample and the methods further include correlating the measured concentration of saccharide in the biological sample to the gastrointestinal permeability in the individual.

Disclosed herein are boronic acid receptors that have utility both as standalone (one component) fluorescent probes and two-component fluorescent probes that utilize a subject boronic acid receptor that has the dual function of a quencher and receptor, and a fluorescent molecule that generates the quantifiable signal to detect saccharides in an aqueous medium. In a subject method with the receptor compound as a one-component fluorescent probe, upon the recognition event with a saccharide or a saccharide derivative, a charge-neutralization event occurs, which in turn causes a perturbation in the chromophoric properties in the naphthalene moiety, enhancing the fluorescence intensity. Without being bound to any particular theory, it is hypothesized that an internal charge transfer-like (ICT-like) process upon addition of a saccharide may be the reason for the increased fluorescence in a one-component system. In a subject method with the receptor compounds in a two component system, the fluorophore can be chosen without affecting the receptor. Such two component systems have been previously developed and translated for practical uses such as continuously measuring glucose levels in the blood in patients (Peyser T, Zisser H, Khan U, Jovanovic L, Bevier W, Romey M, Suri J, Strasma P, Tiaden S, Gamsey S. Use of a novel fluorescent glucose sensor in volunteer subjects with type 1 diabetes mellitus. J Diabetes Sci Technol. 2011; 5(3):687-93; Thoniyot P, Cappuccio F E, Gamsey S, Cordes D B, Wessling R A, Singaram B. Continuous glucose sensing with fluorescent thin-film hydrogels. 2. Fiber optic sensor fabrication and in vitro testing. Diabetes Technology & Therapeutics. 2006; 8(3):279-87).

The previously reported two component system relies on the cationic nature of the receptor compound to form a non-fluorescent ground state complex with the anionic fluorescent dye, 8-hydroxypyrene, 1,3,6-trisulfonic acid trisodium salt (HPTS), and a boronic acid-appended viologen (BBV) that acts dually as a quencher and receptor. In the absence of sugar, a ground state complex is formed due to the coulombic attraction between the anionic dye and cationic quencher with a decrease of fluorescence intensity as compared with free HPTS. When a saccharide binds, the boronic acids are converted to tetrahedral anionic boronate ester, which neutralizes the cationic viologen, diminishing its quenching efficiency and liberating HPTS. The fluorescent signal generated upon dissociation of the ground state complex is directly proportional to sugar concentration. Based on previous work, it was demonstrated that the 4,4'-o-BBV bidentate receptor exhibited unique behavior due to the ortho substitution of the boronic acid motif. The boronic acid is in closer proximity to the quaternary nitrogen and able to participate in a favorable electrostatic interaction (Gamsey, S.; Baxter, N. A.; Sharrett, Z.; Cordes, D. B.; Olmstead, M. M.; Wessling, R. A.; Singaram, B., *Tetrahedron* 2006, 62 (26), 6321-6331). This has been previously documented in work by Lakowicz and co-workers, where a similar interaction was proposed and characterized as a "charge neutralization stabilization mechanism" (Badugu, R.; Lakowicz, J. R.; Geddes, C. D., *Talanta* 2005, 65 (3), 762-768; Arimori, S.; Murakami, H.; Takeuchi, M.; Shinkai, S., *Journal of the Chemical Society-Chemical Communications* 1995, (9), 961-962).

Studies of several boronic acid appended viologens that possess both bipyridinium or phenanthrolinium cores have been previously reported. The ability of these viologens to quench the fluorescence of various anionic reporters has been investigated with these types of compounds and demonstrated that where there is a large number of cationic groups significant quenching was observed (Suri, J. T.; Cordes, D. B.; Cappuccio, F. E.; Wessling, R. A.; Singaram, B., *Langmuir* 2003, 19 (12), 5145-5152; Cappuccio, F. E.; Suri, J. T.; Cordes, D. B.; Wessling, R. A.; Singaram, B., *J. Fluoresc.* 2004, 14 (5), 521-533; Cordes, D. B.; Miller, A.; Gamsey, S.; Sharrett, Z.; Thoniyot, P.; Wessling, R.; Singaram, B., *Organic & Biomolecular Chemistry* 2005, 3 (9)).

The presently disclosed boronic acid appended naphthyl-pyridinium receptors alleviate the need to have a large number of cationic groups. The subject receptors improve on previous receptor compounds abilities to 1) quench the fluorescence of an anionic reporter and 2) improve the sensitivity for the recognition of sugars and sugar derivatives. Further, the subject boronic acid appended naphthyl-pyridinium receptor compounds have been demonstrated to have use both as discrete one-component fluorophore-receptor compounds, and in a two component system coupled to a fluorophore, including but not limited to HPTS and TSPP. The combination of exemplary boronic acid receptor compounds and HPTS or TSPP (receptor-dye) was demonstrated to recognize a number of various sugars and sugar derivatives.

As disclosed herein, a diverse class of boronic acid receptors have been developed that are specific for clinically relevant saccharide biomarkers and provide a low-cost, user-friendly high throughput platform to measure these biomarkers in biological or environmental samples (e.g. urine or waste water). In some cases, the method is a method of measuring the concentration of a saccharide in a sample, the method comprising, contacting the sample with a boronic acid receptor as described herein; measuring the fluorescence emission of the contacted sample, and correlating the extent of fluorescence emission to the concentration of the saccharide in the sample.

In other cases, the method is a method of measuring the concentration of a saccharide in a sample, comprising, contacting the sample with a fluorophore coupled to a subject boronic acid derivative, measuring the fluorescence emission of the contacted sample, and correlating the extent of fluorescence emission to the concentration of the saccharide in the sample.

In some embodiments of the methods disclosed herein, the saccharide is a halogenated saccharide and the method first comprises modifying the halogenated saccharide to generate the corresponding hydroxyl saccharide derivative before contacting with the boronic acid receptor or fluorophore-boronic acid receptor combination as described herein.

In certain embodiments of the methods, the fluorophore is an anionic fluorescent dye. In some cases, the fluorophore is a pyrene sulfonate compound. In certain cases, the fluorophore is 8-hydroxypyrene-1,3,6-trisulfonic acid trisodium salt (HPTS). Several derivatives of HPTS are known and are disclosed in, for example, U.S. Pat. Nos. 7,968,714, and 8,394,357, including but not limited to those in FIGS. 1A-1C. Some derivatives of HPTS include 8-hydroxypyrene-1,3,6-N,N'N"-tris-(methoxypolyethoxyethyl (n~125) sulfonamide (HPTS-PEG); 8-acetoxypyrene-1,3,6-N,N',N"-tris-(methacrylpropylamidosulfonamide) (acetoxy-HPTS-MA); and 8-hydroxypyrene-1,3,6-N,N',N"-tris (carboxypropylsulfonamide) (HPTS-CO$_2$). A generic reference to HPTS in this disclosure can refer to any of these HPTS derivatives. In some cases the fluorophore is tetrakis (4-sulfophenyl) porphine (TSPP). It will be understood that any suitable fluorophore that is able to form the necessary ground state complex with the subject boronic acid receptor may be used in the present methods.

In certain embodiments of the methods, the saccharide or halogenated saccharide is a non-digestible artificial sugar. In certain cases, the saccharide is a non-reducing saccharide. In some cases, the saccharide is selected from the group including, but not limited to, mannitol, sucralose, lactulose, maltitol, lactitol, sorbitol, fructose and tagatose. In some cases, the saccharide is mannitol. In some cases, the saccharide is sucralose. In some cases the saccharide is lactulose. In some cases, the saccharide is maltitol. In some cases, the saccharide is lactitol. In some cases the saccharide is sorbitol. In some cases, the saccharide is fructose. In some cases the saccharide is sucralose.

In some cases of the methods disclosed herein, the halogenated saccharide is sucralose. Sucralose is among the only probes that are used for assessing colonic permeability. Typically, urine is collected from 6 to 24 hours after oral ingestion and urinary excretion is quantified as a percent of the amount ingested.

As outlined above, the present disclosure includes methods of detecting a halogenated disaccharide (e.g., sucralose) in a sample via fluorescence measurement, using a one-component system that comprises a subject boronic acid receptor or a two-component system that comprises a subject boronic acid receptor and a fluorophore. A range of new boronic acid receptors have been synthesized that are stable and require minimal concentrations for uses in the disclosed methods to achieve optimal dynamic range in order to identify saccharide biomarkers of interest.

The disaccharide sucralose is used as a commercial artificial sweetener, which is synthesized by replacing three of the hydroxyl groups on sucrose with chlorine. It is regarded to be 600 times sweeter than sucrose, but is impervious to sucrase hydrolysis. Since it appears in the urine unchanged, it has been utilized widely as a biomarker for measuring small intestinal and colonic permeability. If small intestinal permeability is normal, then it can be used to detect an increase in colonic permeability alone. A common technique for determining the concentrations of these urinary sugars is liquid chromatography/mass spectrometry (LC/MS) in combination with refractive index.

The method of measuring the concentration of a halogenated saccharide in a sample, first requires modification of the halogenated saccharide to generate the corresponding hydroxyl saccharide derivative. To this end, the primary and secondary alkyl halides of sucralose are reacted such that they are replaced by hydroxyl groups and the fructose ring is opened in order to yield a detectable sugar alcohol. Based on literature precedence, sucralose can be modified through advanced oxidation photolysis to generate a sugar alcohol derivative. The methods described herein utilize the Fenton and similar oxidation reactions to generate reactive hydroxyl and radical species in solution to de-chlorinate sucralose to yield a sugar alcohol derivative of the fructose moiety. This modified sugar is quantified using the subject boronic acid receptors with the methods disclosed herein.

Accordingly, in some cases, the halogenated saccharide is modified using a Fenton oxidation reaction to generate the corresponding hydroxyl saccharide derivative. In other cases, the halogenated saccharide is modified using an enzymatic or photolysis approach to generate the corresponding hydroxyl saccharide derivative.

In some embodiments of the methods disclosed herein, the sample is a biological sample or an environmental sample. In certain cases, the biological sample is selected from the group including blood or components thereof, urine, semen, sweat, saliva, tears, and fecal matter. In certain cases, the biological sample is urine. In certain other embodiments, the sample is an environmental sample, including but not limited to a waste water sample.

In some embodiments, the sample is a biological sample obtained from an individual, and the method further comprises correlating the measured concentration of a saccharide in the biological sample to the gastrointestinal permeability in the individual.

Proper gastrointestinal (GI) function is critical for absorption of nutrients, a process that is facilitated by the absorptive area of the GI. The only way to noninvasively assess GI function is to perform a permeability test. Normally, human GI permeability is assessed by the measurement of urinary excretion of an orally administered disaccharide (lactulose, sucrose, or sucralose) and a monosaccharide (mannitol or L-rhamnose). The urinary excretion of these biomarkers is considered to be a parameter of gastrointestinal health. A common technique for determining the concentrations of these urinary sugars is performance liquid chromatography/mass spectrometry (LC/MS) in combination with refractive index (Miki K, Butler R, Moore D, Davidson G. Rapid and simultaneous quantification of rhamnose, mannitol, and lactulose in urine by HPLC for estimating intestinal permeability in pediatric practice. Clinical Chemistry. 1996; 42(1): 71-5).

High throughput assays are becoming indispensable for studying biological processes and discovering novel compounds for potential new drug candidates. Aside from studying biological processes and discovering potent compounds, there is an increasing utility for high throughput assays in clinical chemistry. Whether it is looking for biomarkers in blood serum or urine, there are still certain assays that could be done more rapidly and effectively. One instance is a permeability test. These tests look at the gastrointestinal tract permeability to provide insight on GI barrier function.

Such tests are routinely used in clinical research because of their noninvasiveness and usefulness as tools to investigate the role of increased permeability in such disorders as inflammatory bowel disease (IBD) (Crohn's disease and ulcerative colitis), Parkinson's disease, celiac disease, and diabetes mellitus, to name a few.

Rapid quantification of saccharide biomarkers enables gastrointestinal permeability tests for routine use. The methods disclosed herein equip clinicians to use the permeability test routinely to monitor the GI permeability of patients who have undergone GI procedures. Such testing is of value in pharmacological studies of drug absorption and bioavailability of pharmaceuticals that affect GI permeability.

In some cases, the sample is a biological sample obtained from an individual and the individual has ingested one or more saccharides over a period of 0 to 24 hours before the biological sample is obtained. In some cases, the individual has ingested one or more saccharides 3, 6, 9, 12, 18 or 24 hours before the sample is obtained. In certain cases, the individual has ingested a known quantity of one or more saccharides.

In broad terms, an individual may consume a known quantity of a saccharide, preferably a non-metabolizable saccharide. After a certain amount of time, a fluid, for example urine, is obtained from the individual. The fluid is then contacted with a solution having a subject boronic acid receptor by itself (a one-component system) or coupled to a fluorophore (a two-component system). In the subject two component system for example, the boronic acid receptor quenches the fluorescence of the fluorophore. When one or more particular saccharides are present, the boronic acid receptor binds the disaccharide and loses its ability to quench the fluorophore. The more saccharide that is present in the solution, the more fluorescent the solution is. By comparing the fluorescence obtained from an unknown sample, and comparing the fluorescence to a series of standards, the concentration of the saccharide in the solution may be determined. If one knows how much saccharide was consumed, then one is able to measure the extent of the permeability of the gastrointestinal tract.

In some embodiments, the individual ingests riboflavin simultaneously with the one or more saccharides. In certain cases, the fluorescence measurement of the amount of a saccharide in the sample is normalized against riboflavin fluorescence in the same sample.

Riboflavin has been found to be almost entirely absorbed through the type 2 riboflavin transporter (RFT2) at apical epithelial membranes in the small intestine. Loss of RFT2 expression results in severe riboflavin deficiency. Hence, appearance of riboflavin in urine after oral ingestion reflects absorption at duodenum and jejunum in the small intestine. Riboflavin's intrinsic fluorescence suggests a methodological advantage while reflecting absorption of an actual nutrient.

In some embodiments, riboflavin fluorescence, reflecting transcellular absorptive capacity of villi in the small intestine, is used to normalize the fluorescence measurement of the amount of a saccharide in a sample. In some embodiments, riboflavin is confined to uptake through the Riboflavin Transporter 2 (RFT2) and correlates more strongly with condition of villi tips of duodenum and jejunum. In some embodiments, wherein RFT2 transport is down-regulated in gastrointestinal diseases, riboflavin measurements serve to identify such conditions.

In some embodiments of the methods disclosed herein, the biological sample is urine. In some embodiments, the urine sample is collected from the subject at regular intervals after ingestion of the sugar and/or riboflavin. In some embodiments, the urine sample is collected for 3, 6, 9, 12, 18, 24 hours, or any other time in between, at regular intervals after ingestion of the sugar and/or riboflavin.

In some embodiments of the methods disclosed herein, the subject boronic acid receptor is present in a concentration of 500 μM or less, such as 450 μM, 400 μM, 350 μM, 300 μM, 250 μM, 200 μM or 150 μM. In some cases, subject boronic acid receptor is present in a concentration of 150 μM or less, such as 125 μM, 100 μM, 75 μM, 50 μM or even less.

In certain embodiments of the two-component methods disclosed herein, to achieve about 80% of quenched fluorescence 150 μM or less of each quencher (boronic acid receptor compound) was needed. In some cases, to achieve 80% of quenched fluorescence less than 150 μM of each quencher was need, such as 125 μM, 100 μM, 75 μM, 50 μM or even less. In some embodiments of the two-component methods disclosed herein, the ratio of the subject boronic acid receptor compound (quencher) to the fluorophore (e.g. anionic dye) is 100:1 or less, such as 75:1, 50:1, 25:1 or even less. In certain cases of the two-component methods disclosed herein, the ratio of the boronic acid receptor compound (quencher) to the fluorophore (e.g. anionic dye) is 25:1 or less, such as 22:1, 20:1, 18:1, 16:1, 14:1, 12:1, 10:1 or even less. In some cases, the optimal ratio of the boronic acid receptor compound (quencher) to the fluorophore (e.g. anionic dye) is 100:1. In some cases, the optimal ratio of the boronic acid receptor compound (quencher) to the fluorophore (e.g. anionic dye) is 50:1. In some cases, the optimal ratio of the boronic acid receptor compound (quencher) to the fluorophore (e.g. anionic dye) is 20:1. In other cases, the optimal ratio of the boronic acid receptor compound (quencher) to the fluorophore (e.g. anionic dye) is 18:1.

Kits

Aspects of the invention further include kits for use in practicing the subject methods. The receptor compounds of the invention can be included as reagents in kits for use in, for example, the methodologies described above.

A kit can include a solution of boronic acid receptor (e.g., as described herein), a buffer, and instructions for use, wherein the solution is distributed into the wells of one or more microtiter plates. In certain cases, the boronic acid receptor is a compound of any one of structures 1 to 11.

In certain embodiments, the kit further comprises a fluorophore. the fluorophore is an anionic dye. In some cases, the fluorophore is HPTS. In certain other cases, the fluorophore is TSPP.

In certain embodiments of the kits disclosed herein, the buffer is 4× premix buffer.

The term "microtiter plate" as used herein refers to a flat plate with multiple wells used as small test tubes. Examples of the number of wells include, but are not limited to, 6, 24, 96, 384, 1536, 3456, or 9600 wells. In one embodiment, the volume of this reagent solution prior to addition of biological fluid in each well is 10 μL.

In some embodiments, the microtiter plates are covered with adhesive tape. In certain embodiments, the fluorescence assay kit is stored at between 2° C. and 15° C., most preferably at 4° C. In one embodiment, the kit comprises a solution with 1.0 to 2.0 mM of a subject boronic acid, 10 to 20 μM HPTS, 100 mM 4-(2-Hydroxyethyl)piperazine-1-ethanesulfonic acid (HEPES), 100 mM sodium phosphate, and 0.04% w/v Triton X-100 at pH 7.4.

In some embodiments, the kit further comprises a buffer solution for blank subtraction. In some embodiments, the buffer solution comprises HEPES, sodium phosphate and Triton X-100. In one embodiment, the buffer solution comprises the 4× premix buffer. In some embodiments, the buffer solution further comprises a fluorophore. In some embodiments, the buffer solution further comprises a fluorescence quencher. In some embodiments, the fluorescence quencher is a boronic acid receptor as disclosed herein.

In other embodiments, the one or more components of the kit may be provided in separate containers (e.g., separate tubes, bottles, or wells in a multi-well strip or plate). The boronic acid receptors of the kit may be provided in a liquid composition, such as any suitable buffer as described above. Alternatively, the boronic acid receptors of the kit may be provided in a dry composition (e.g., may be lyophilized), and the kit may optionally include one or more buffers for reconstituting the dry compound. In certain aspects, the kit may include aliquots of the boronic acid receptors provided in separate containers (e.g., separate tubes, bottles, or wells in a multi-well strip or plate).

In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The boronic acid receptors, methods and kits as described herein may find use in a variety of applications, including analysis of various biological samples or water samples, in which the detection and/or quantification of one or more saccharides is desirable. Methods of the invention find use in a variety of different applications including any convenient application where detection and/or quantitation of saccharides by fluorescence is of interest. In some instances, the subject receptors find use in detecting and/or quantifying the level of one or more saccharides in an aqueous sample. Such aqueous samples may include but are not limited to, an environmental water sample, a treated or untreated waste water sample and drinking water sample. In other instances, the subject receptors find use in detecting and/or quantifying the level of one or more saccharides in a biological fluid e.g. urine.

In some instances, the subject methods find use in rapid and high throughput chemical assays that quantify the concentration of particular saccharides for evaluating the gastrointestinal (GI) tract permeability, and thus provide insight on GI barrier function. Such tests may be used routinely in clinical research because of their noninvasiveness and usefulness as tools to investigate the role of increased permeability in such disorders as inflammatory bowel disease (IBD) (Crohn's disease and ulcerative colitis), Parkinson's disease, celiac disease, and diabetes mellitus.

ADDITIONAL EMBODIMENTS

Additional embodiments are set forth in the following clauses.

Clause 1. A boronic acid receptor of formula (I):

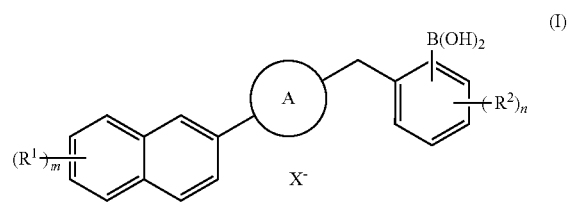

wherein:

is selected from,

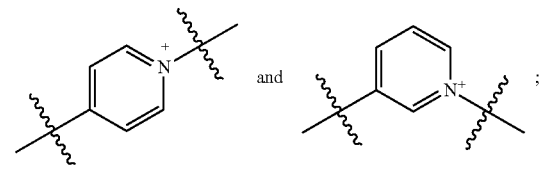

$R^1$ and $R^2$ are independently selected from an alkaryl group, a substituted alkaryl group, an aralkyl group, a substituted aralkyl group, an aryl group, a substituted aryl group, a heteroaryl group, a substituted heteroaryl group, a heteroaryl cation, a substituted heteroaryl cation, heterocycle group, a substituted heterocycle group;

n and m are independently an integer from 0 to 4; and $X^-$ is a counter ion, wherein the number of counter ions is equivalent to the number of cations in the receptor.

Clause 2. The boronic acid receptor of clause 1, wherein

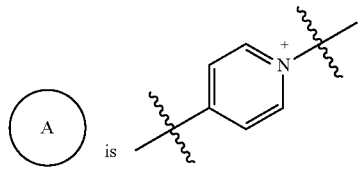

Clause 3. The boronic acid receptor of clause 1, wherein

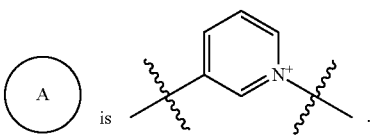

Clause 4. The boronic acid receptor according to any one of clauses 1 to 3, wherein formula (I) has the structure of formula (IA) or (IB):

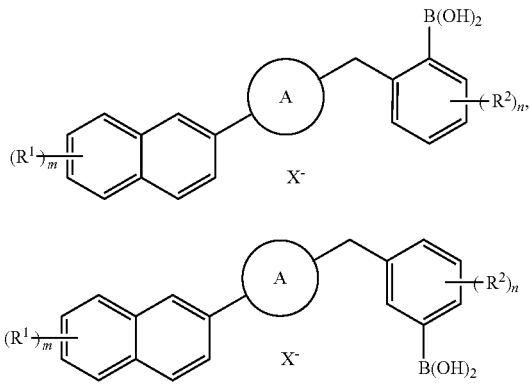

wherein:

is selected from,

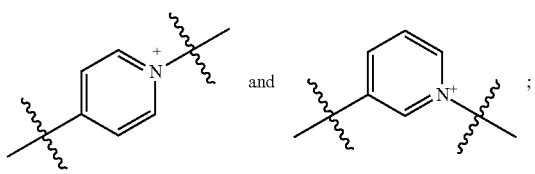

$R^1$ and $R^2$ are independently selected from an alkaryl group, a substituted alkaryl group, an aralkyl group, a substituted aralkyl group, aryl group, a substituted aryl group, a heteroaryl group, a substituted heteroaryl group, a heteroaryl cation, a substituted heteroaryl cation, heterocycle group, a substituted heterocycle group;

n and m are independently an integer from 0 to 4; and $X^-$ is a counter ion, wherein the number of counter ions is equivalent to the number of cations in the receptor.

Clause 5. The boronic acid receptor according to any one of clauses 1 to 4, wherein m is 0, n is 1 and $R^2$ is a substituted heteroaryl cation group.

Clause 6. The boronic acid receptor according to any one of clauses 1 to 4, wherein n is 0, m is 1 and $R^1$ is a substituted heteroaryl cation group.

Clause 7. The boronic acid receptor of clause 5 or 6, wherein the heteroaryl cation group is substituted with a group selected from, boronic acid, an aryl group, and an aryl substituted with a boronic acid group.

Clause 8. The boronic acid receptor according to any one of clauses 1 to 4, wherein $R^1$ and $R^2$ are independently selected from:

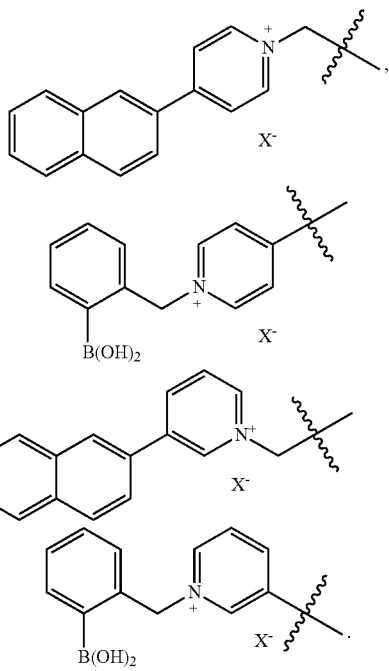

Clause 9. The boronic acid receptor according to any one of clauses 1 to 8, wherein $X^-$ is a halogen.

Clause 10. The boronic acid receptor according to any one of clauses 1 to 9, wherein the number of cations and counter ions are each two.

Clause 11. The boronic acid receptor according to any one of clauses 1 to 10, wherein formula (I) is a structure selected from:

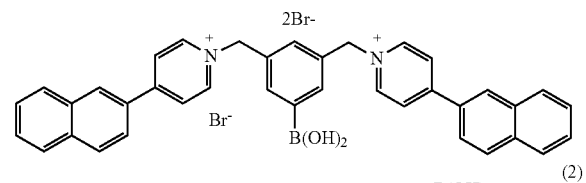

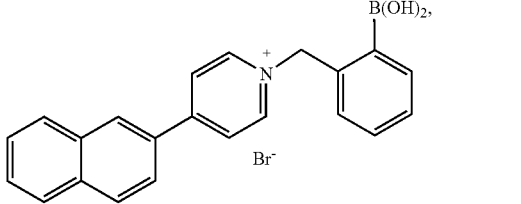

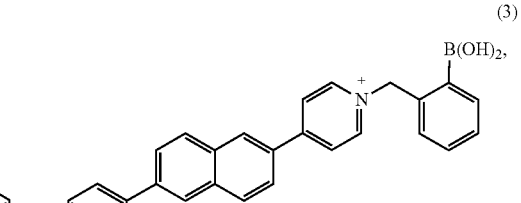

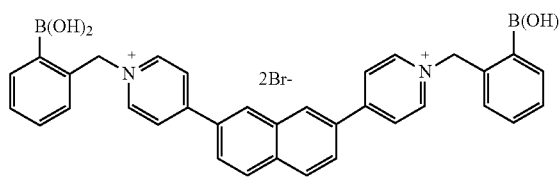

(4)

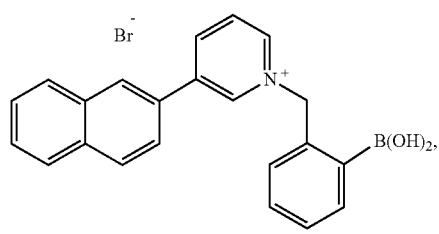

(5)

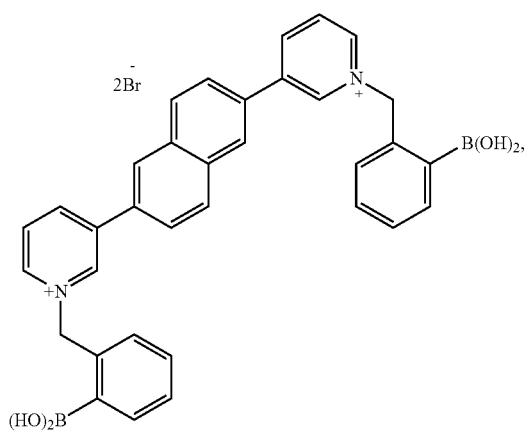

(6)

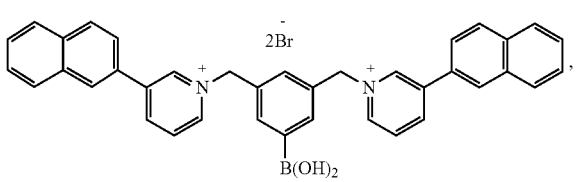

(7)

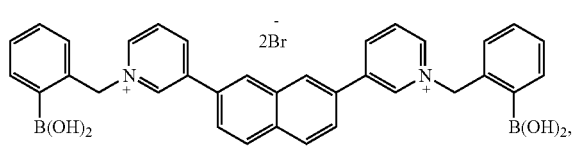

(8)

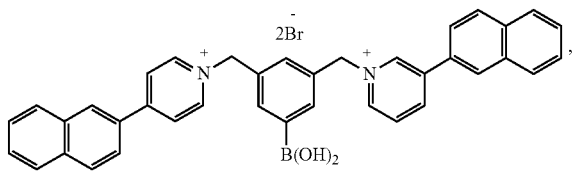

(9)

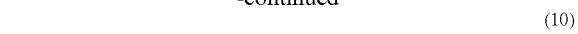

(10)

and (11)

Clause 12. A method of measuring the concentration of a saccharide in a sample, the method comprising:

contacting the sample with a boronic acid receptor according to any one of clauses 1 to 11;

measuring the fluorescence emission of the contacted sample; and correlating the extent of fluorescence emission to the concentration of the saccharide in the sample.

Clause 13. A method of measuring the concentration of a saccharide in a sample, the method comprising:

contacting the sample with a fluorophore coupled to a boronic acid derivative according to any one of clauses 1 to 11;

measuring the fluorescence emission of the contacted sample; and correlating the extent of fluorescence emission to the concentration of the saccharide in the sample.

Clause 14. The method of clause 12 or 13, wherein the saccharide is a halogenated saccharide and the method first comprises:

modifying the halogenated saccharide to generate the corresponding hydroxyl saccharide derivative.

Clause 15. The method of clauses 13 or 14, wherein the fluorophore is an anionic fluorescent dye.

Clause 16. The method of clause 15, wherein the fluorophore is 8-hydroxypyrene-1,3,6-trisulfonic acid trisodium salt (HPTS) or tetrakis (4-sulfophenyl) porphine (TSPP).

Clause 17. The method according to any one of clauses 12 to 16, wherein the saccharide is a non-digestible artificial sugar.

Clause 18. The method of clause 14, wherein the halogenated saccharide is sucralose.

Clause 19. The method of clause 14, wherein the halogenated saccharide is modified using a Fenton oxidation reaction to generate the corresponding hydroxyl saccharide derivative.

Clause 20. The method of clause 14, wherein the halogenated saccharide is modified using an enzymatic or photolysis approach to generate the corresponding hydroxyl saccharide derivative.

Clause 21. The method of clause 12 or 13, wherein the saccharide is selected from the group consisting of, mannitol, lactulose, maltitol and lactitol, sorbitol, fructose and tagatose.

Clause 22. The method according to any one of clauses 12 to 21, wherein the sample is a biological sample or an environmental sample.

Clause 23. The method of clause 22, wherein the sample is a biological sample selected from the group consisting of blood or components thereof, urine, semen, sweat, saliva, tears, and fecal matter.

Clause 24. The method according to any one of clauses 12 to 23, wherein the sample is a biological sample obtained from an individual, and the method further comprises correlating the measured concentration of a saccharide in the biological sample to the gastrointestinal permeability in the individual.

Clause 25. The method according to any one of clauses 12 to 24, wherein the sample is a biological sample obtained from an individual and the individual has ingested one or more saccharides over a period of 0 to 24 hours before the biological sample is obtained.

Clause 26. The method of clause 25, wherein the individual has ingested a known quantity of one or more saccharides.

Clause 27. The method of clause 25 or clause 26, wherein the subject ingests riboflavin simultaneously with the one or more saccharides.

Clause 28. The method according to any one of clauses 12 to 27, wherein the fluorescence measurement of the amount of saccharide in the sample is normalized against riboflavin fluorescence in the same sample.

Clause 29. A fluorescence assay kit comprising a solution of a boronic acid receptor of any one of clauses 1 to 11, a buffer, and instructions for the use of the kit, wherein the solution is distributed into the wells of one or more microtiter plates.

Clause 30. The fluorescence assay kit of clause 29, further comprising a fluorophore.

Clause 31. The fluorescence assay kit of clause 29 or 30, wherein the buffer is 4× premix buffer.

Clause 32. The fluorescence assay kit according to any one of clauses 29 to 31, wherein the boronic acid chemoreceptor is a compound of clause 11.

Clause 33. The fluorescence assay kit according to any one of clauses 30 to 32, wherein the fluorophore is HPTS or TSPP.

EXAMPLES

Example 1: Synthesis of Boronic Acid Receptors

The synthesis of the subject boronic acid appended naphthyl-pyridinium receptor compounds was obtained via Suzuki-Miyaura coupling using a modified version of previously reported procedures followed by nucleophilic substitution with the appropriate bromomethyl phenyl boronic acid. The synthesis of 2-(3,5-bis(bromomethyl)phenyl)-1,3,2-dioxaborinane was followed according to published procedure (Suri, J. T.; Cordes, D. B.; Cappuccio, F. E.; Wessling, R. A.; Singaram, B., *Angewandte Chemie-International Edition* 2003, 42 (47), 5857-5859). The synthetic scheme to exemplary receptor compounds 1-4 is shown in FIG. 1.

Synthesis of 4-naphthalenyl pyridine-(a): In a 3-neck round bottom flask (25 mL) purged with nitrogen, a solution containing tetrakis (triphenylphosphine) palladium (0.034 g, 0.03 mmol), CsCO$_3$ (0.423 g, 1.2 mmol), and 4-pyridinyl boronic acid (0.147 g, 1.2 mmol) in DMF (7 mL) was mixed and allowed to stir for 30 minutes at 25° C. 1-bromonaphthalene (0.140 mL, 1 mmol) was added and the mixture stirred at 100° C. for 24 h. After cooling to room temperature, the mixture was washed with deionized water (30 mL) and extracted with DCM (3×15 mL). The organic fraction was dried with MgSO$_4$ and concentrated in a slurry of silica and further purified by flash chromatography with a mixture 2:1 of Hex:EtOAc/EtOH (3:1) as eluent to give the title compound as a white amorphous solid (0.131 g, 64% yield). $^1$H NMR (400 MHz, Chloroform-d) δ 8.77-8.70 (m, 2H), 8.00-7.90 (m, 2H), 7.94-7.80 (m, 2H), 7.55 (dd, J=8.3, 7.0 Hz, 2H), 7.55-7.43 (m, 2H), 7.48-7.38 (m, 4H); $^{13}$C NMR (101 MHz, Chloroform-d) δ 150.33, 149.81, 148.66, 137.34, 133.74, 130.72, 128.84, 128.50, 126.84, 126.62, 126.15, 125.32, 125.15, 125.01, 121.83. C$_{15}$H$_{11}$N [M+H]$^+$: 206.093, found 206.100. (Karagiaridi, O.; Bury, W.; Tylianakis, E.; Sarjeant, A. A.; Hupp, J. T.; Farha, O. K., *Chemistry of Materials* 2013, 25 (17), 3499-3503).

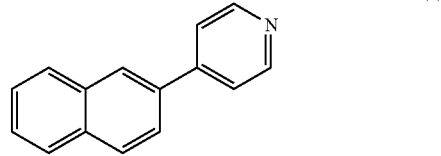

(a)

Synthesis of 2,6-dipyridinyl naphthalene-(b): To an oven dried 3-neck round bottom flask (25 mL) purged with argon, was added Pd(OAc)$_2$ (0.018 g, 0.08 mmol, 4 mol %), XPhos (0.046 g, 0.096 mmol, 4.8 mol %), 2,6-dibromonaphthalene (0.570 g, 2 mmol), 4-pyridinyl boronic acid (0.540 g, 4.4 mmol), and 1,4-dioxane (11.2 mL). After the mixture pre-stirred at 25° C. for 30 minutes, a degassed aqueous solution of NaOH (2.8 mL, 10.2 mmol, 1.2 M) was added to the mixture and vigorously stirred at 95° C. for 48 h. At the end of the reaction, the organics were extracted with ethyl acetate (2×10 mL) and subsequently washed with deionized water (10 mL×2). The organic layers were dried with MgSO$_4$ and concentrated on a rotary evaporator. A silica slurry was made and was purified by silica gel flash chromatography with a mixture 3:2 of Hex:EtOAc/EtOH (3:1) as eluent to give the title compounds as a white crystalline solid (0.338 g, 59% yield). $^1$H NMR (400 MHz, Chloroform-d) δ 8.78-8.70 (m, 4H), 8.19-8.14 (m, 2H), 8.05 (d, J=8.5 Hz, 2H), 7.82 (dd, J=8.5, 1.7 Hz, 211), 7.69-7.62 (m, 4H); $^{13}$C NMR (101 MHz, CDCl$_3$) δ 150.42, 147.88, 136.37, 133.45, 129.49, 126.21, 125.43, 121.80. HRMS-ESI m/z calculated for C$_{20}$H$_{14}$N$_2$ [M+H]$^+$: 283.119, found 283.100. (Yang, J.; Liu, S.; Zheng, J.-F.; Zhou, J., *European Journal of Organic Chemistry* 2012, (31), 6248-6259).

(b)

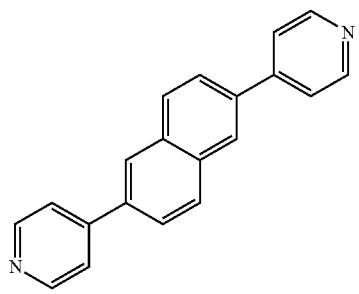

Synthesis of 2,7-dipyridinyl naphthalene-(c): To an oven dried 3-neck round bottom flask (25 mL) purged with nitrogen, was added Pd(OAc)$_2$ (0.018 g, 0.08 mmol, 4 mol %), XPhos (0.046 g, 0.096 mmol, 4.8 mol %), 2,7-dibromonaphthalene (0.570 g, 2 mmol), 4-pyridinyl boronic acid (0.540 g, 4.4 mmol), and 1,4-dioxane (11.2 mL). After the mixture pre-stirred at 25° C. for 30 minutes, a degassed aqueous solution of NaOH (2.8 mL, 10.2 mmol, 1.2 M) was added to the mixture and vigorously stirred at 95° C. for 48 h. At the end of the reaction, the organics were extracted with ethyl acetate (2×10 mL) and subsequently washed with deionized water (10 mL×2). The organic dried with MgSO$_4$ and concentrated on a rotary evaporator. A silica slurry was made and was purified by silica gel flash chromatography with a mixture 3:2 of Hex:EtOAc/EtOH(3:1) as eluent to give the title compounds as a white crystalline solid (0.30 g, 53% yield). $^1$H NMR (400 MHz, Chloroform-d) δ 8.76-8.70 (m, 4H), 8.20 (dt, J=1.6, 0.7 Hz, 2H), 8.01 (dt, J=8.7, 0.8 Hz, 2H), 7.81 (dd, J=8.6, 1.8 Hz, 2H), 7.69-7.61 (m, 4H), 7.57-7.50 (m, 1H); $^{13}$C NMR (101 MHz, Chloroform-d) δ 150.69, 150.42, 147.90, 136.34, 133.56, 133.34, 128.79, 126.88, 125.54, 121.80, 121.37; HRMS-ESI m/z calculated for C$_{20}$H$_{14}$N$_2$[M+H]$^+$: 283.119, found 283.100.

(c)

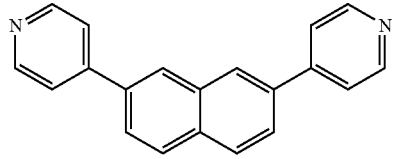

Synthesis of 1,1'-(5-borono-1,3-phenylene)bis(methylenelbis(4-naphthalenyl)pyridinium-(1): Naphtyl pyridine (0.513 g, 2.5 mmol) was added to a solution of 3,5-bis(bromomethyl)phenyl)-dioxaborinane (0.347 g, 1 mmol) in DMF and stirred at 65° C. for 48 h. To the lightly yellow solution, cold acetone was added (20 mL) to induce precipitation of a white solid. The solid was collected by centrifugation, and was washed with acetone. To deprotect the boronic acids, the solid was dissolved in methanol (~10 mL), 12 M HCl (0.5 mL) and heated at 80° C. for 30 min. After cooling to room temperature, the mixture was concentrated and cold acetone was added and stored at 4° C. for 2 h. The solid was then collected, washed with acetone, and dried under a stream of nitrogen to afford a white solid (0.524 g, 73% yield). $^1$H NMR (400 MHz, Methanol-d$_4$) δ 9.26-9.11 (m, 4H), 8.33-8.24 (m, 4H), 8.13-7.86 (in, 911), 7.70-7.52 (m, 811), 6.03 (s, 4H); $^{13}$C NMR (101 MHz, Methanol-d$_4$) δ 158.32, 144.44, 134.07, 133.95, 133.42, 131.29, 129.60, 129.04, 128.70, 128.37, 127.66, 126.59, 125.16, 123.52, 63.27. HRMS-ESI m/z calculated for C$_{22}$H$_{19}$BNO$_2$ [M-2Br]$^+$: 340.151, found 340.200.

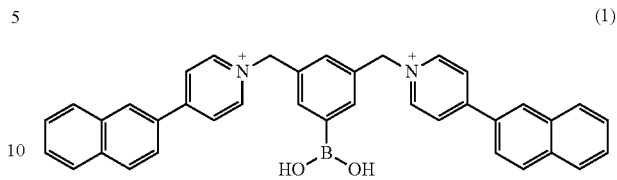

(1)

Synthesis of 1-(2-boronobenzyl)-4-(naphthalen-2-yl)pyridinium bromide-(2): To a solution of 2-bromomethylphenyl boronic acid (0.3 g, 3.6 mmol) in DMF (10 mL) was added, 4-naphtyl pyridine (0.846 g, 3 mmol), and the reaction was stirred at 65° C. for 48 hours. The reaction mixture was cooled to room temperature DCM (25 mL) and the organics were washed with deionized water (3×15 mil) and set aside. The aqueous fraction was frozen and the water was removed via lyophilization. Yellow solid was obtained and subsequently washed with cold acetone before collecting. The solid was centrifuged, collected, and dried under a stream of nitrogen (0.611 g, 48% yield). $^1$H NMR (400 MHz, DMSO-d$_6$) δ 9.16-9.09 (m, 2H), 8.36-8.29 (m, 2H), 8.20-8.06 (m, 2H), 7.93 (s, 1H), 7.87-7.79 (m, 2H), 7.72-7.57 (m, 3H), 7.55-7.41 (m, 2H), 6.10 (s, 2H); $^{13}$C NMR (101 MHz, DMSO-d$_6$) δ 156.70, 145.08, 138.12, 135.85, 134.07, 133.77, 131.40, 130.96, 130.36, 129.77, 129.30, 129.11, 128.94, 128.88, 128.24, 127.29, 126.09, 124.51, 63.43. HRMS-ESI m/z calculated for C$_{22}$H$_{19}$BNO$_2$ [M-Br]$^+$: 340.151, found 340.200.

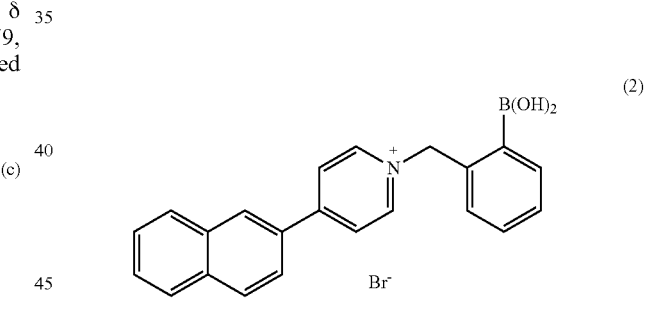

(2)

Synthesis of 4,4'-(naphthalene-2,6-diyl)bis(1-(2-boronobenzyl) pyridinium-(3): To a solution of 2-bromomethylphenyl boronic acid (0.451 g, 2.1 mmol) in DMF (7 mL) was added, 2,6-dipyridinyl naphthalene (0.282 g, 1 mmol), and the reaction was stirred at 65° C. for 48 hours. The reaction mixture was cooled to room temperature and cold acetone (25 mL) was added to induce further precipitation of a pale yellow solid. The precipitate was centrifuged, washed with acetone (3×20 mL) and dried under a stream of nitrogen (0.571 g, 79©% yield). $^1$H NMR (400 MHz, DMSO-d$_6$) δ 9.16-9.09 (m, 4H), 8.86 (d, J=1.8 Hz, 2H), 8.73-8.64 (m, 4H), 8.52 (s, 4H), 8.32 (d, J=8.7 Hz, 2H), 8.25 (dd, J=8.7, 1.8 Hz, 2H), 7.86-7.78 (in, 211), 7.53-7.39 (m, 411), 7.32 (dd, J=7.7, 1.4 Hz, 211), 6.05 (s, 411); $^{13}$C NMR (101 MHz, DMSO-d$_6$) δ 154.70, 145.49, 138.38, 134.41, 133.49, 131.08, 130.92, 129.76, 129.39, 125.40, 63.74. HRMS-ESI m/z calculated for C$_{34}$H$_{30}$B$_2$N$_2$O$_4$[M+1]$^+$: 551.253, found 551.200.

(3)

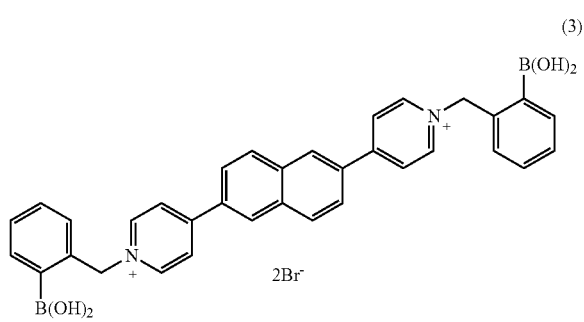

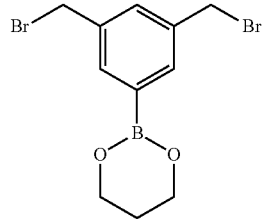

Synthesis of 4,4'-(naphthalene-2,7-diyl)bis(1-(2-boronobenzyl) pyridinium-(4) To a solution of 2-bromomethylphenyl boronic acid (0.473 g, 2.2 mmol) in DMF (7 mL) was added, 2,7-dipyridinyl naphthalene (0.282 g, 1.1 mmol), and the reaction was stirred at 65° C. for 48 hours. The reaction mixture was cooled to room temperature and cold acetone (25 mL) was added to induce further precipitation of a pale yellow solid. The precipitate was centrifuged, washed with acetone (3×20 mL) and dried under a stream of nitrogen (0.685 g, 87% yield). $^1$H NVR (400 MHz, DMSO-dc) a 9.12 (d, J=6.3 Hz, 4H), 8.85 (d, J=3.3 Hz, 2H), 8.68-8.60 (m, 4H), 8.52 (bs, 4H), 8.33-8.24 (m, 4H), 7.87-7.77 (m, 2H), 7.55-7.40 (m, 4H), 7.33 (d, J=7.5 Hz, 2H), 6.05 (s, 4H); $^{13}$C NMR (101 MHz, DMSO-d$_6$) δ 154.75, 145.51, 138.32, 135.88, 135.75, 133.09, 132.61, 130.92, 130.55, 129.89, 128.84, 127.22, 125.31, 63.27. HRMS-ESI m/z calculated for $C_{34}H_{30}B_2N_2O_4$ [M+H]$^+$: 551.253, found 551.200.

(4)

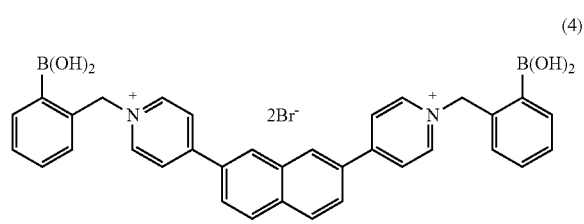

Synthesis of 2-(3,5-bis(bromomethyl)phenyl-1,3,2-dioxaborinane: To a 100 mL round bottom flask fitted with a condenser and a sidearm was added 3,5-dimethyl phenyl boronic acid (1.5 g, 10 nmol), calcium hydride (0.843 g, 20 mmol), and dichloroethane (50 mL). After 10 minutes of stirring under nitrogen, 1,3 propanediol (0.80 mL, 11 mmol) was added via syringe. The reaction was refluxed for 2 h, cooled to room temperature, and filtered. The filtrate was mixed with N-bromosuccinimide (3.91 g, 22 mmol) and 2,2'-azobisisobutyronitrile (0.328 g, 2 mmol) and refluxed for 3 h. The orange solution was cooled overnight, and the succinate crystals were filtered off. The filtrate was concentrated leaving an off-white solid, which was recrystallized from methanol (1.5 g, 45% yield). $^1$H NMR (400 MHz, Chloroform-d) δ 7.72 (d, J=1.9 Hz, 211), 7.47 (t, J=1.9 Hz, 1H), 4.48 (s, 411), 4.21-4.14 (m, 4H), 2.04 (q, 1=5.5 Hz 2H); $^{13}$C NMR (101 MHz, Chloroform-d) δ 137.56, 134.33, 131.73, 62.04, 33.15, 27.36.

Example 2: Absorption and Emission Properties of Boronic Acid Receptors

Absorption measurements of exemplary boronic acid receptor compounds: All absorption measurements were carried out using an Agilent Technologies Cary 60 Vis instrument in a quartz cuvette (1 cm pathlength). Stock solutions (1 mg/mL) of each compound was initially prepared in DMSO and then diluted to the desired concentration in 0.1 M sodium phosphate buffer pH 7.4 which gave minimal DMSO amount of at least 15%. Concentrations for each boronic acid receptor in cuvette are as follows; (1)=100 μM, (2)=100 μM, (3)=50 μM, and (4)=50 M. Measurements were done in situ by taking the absorbance of each receptor compound in phosphate buffer pH 7.4, then aliquots of buffered 1 M lactulose (0.5-7 μL) was added, shaken for 30 seconds, and the new absorbance was recorded.

Fluorescence Measurements of exemplary boronic acid receptor compounds: Stock solutions of each boronic acid receptor compound (1-4) were initially prepared in DMS (1 mg/mL) and then diluted to desired initial 1 mM concentration before adding to the wells. Each lactulose concentration points were prepared in 0.1 M sodium phosphate buffer as 2-fold of the desired final concentration in each well. Each well received 20 μL of each receptor compound and sugar concentration (each data point recorded in triplicates) and the fluorescence measurements were conducted in a 96-well plate (Corning #3694) using a Tecan infinite M1000 instrument a plate reader (gain 100, flashes 30, z-position 1.8 cm) Plates were shaken for 30 seconds (2 mm orbital amplitude) prior to reading.

Exemplary compounds were examined for their absorbance changes to demonstrate their ability to undergo photophysical changes upon recognition of a sugar. A representative absorption and emission spectra for exemplary compounds 1-4 with increasing amounts of lactulose in buffer solution are shown in FIG. 3, panels A to D, and FIG. 4, panels A to D, respectively.

Figure 3:
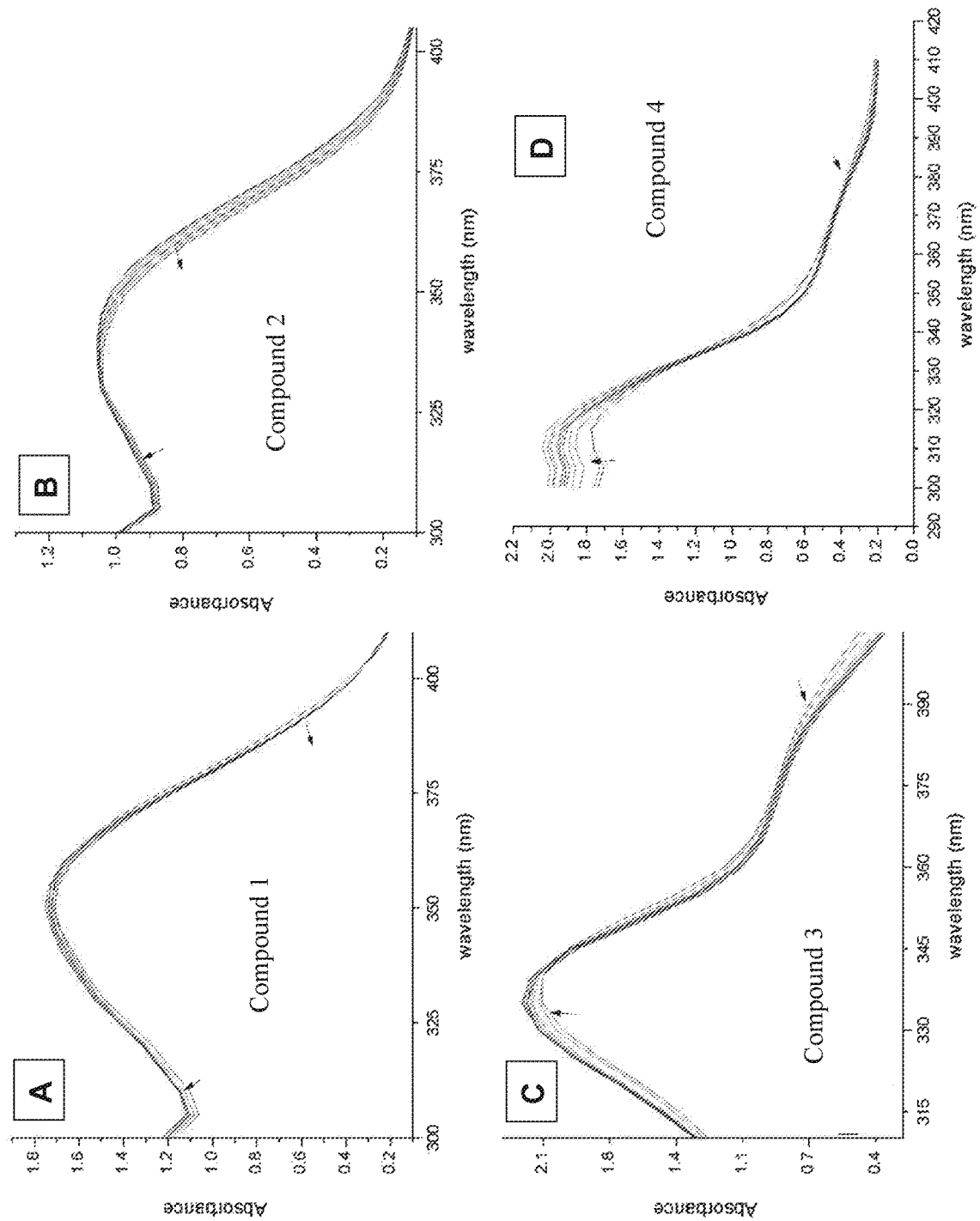
FIG. 3, panels A to D, show the absorption spectra of exemplary boronic acid receptor compounds (1-4) with an increasing amount of lactulose.

With reference to FIG. 3, panels A to D, change of absorbance for each receptor compound was monitored as a function of increasing lactulose. Incremental changes of absorbance were observed with increasing amounts of lactulose for each of compounds 1-4. Each compound provided absorbance maxima between 300-350 nm and with isosbestic points between 330-350 nm for all four receptors. Additionally, the compounds provided molar extinction coefficients of $1.17 \times 10^4$ (100 μM), $1.10 \times 10^4$ (100 μM), $2.77 \times 10^4$ (50 μM), and $5.01 \times 10^4$ (50 μM) M$^{-1}$ cm$^{-1}$ for 1-4 respectively. Without being bound to any particular theory, these absorption changes upon sugar binding at physiological pH for compounds 1-4 is indicative of a possible charge transfer process.

Figure 4:
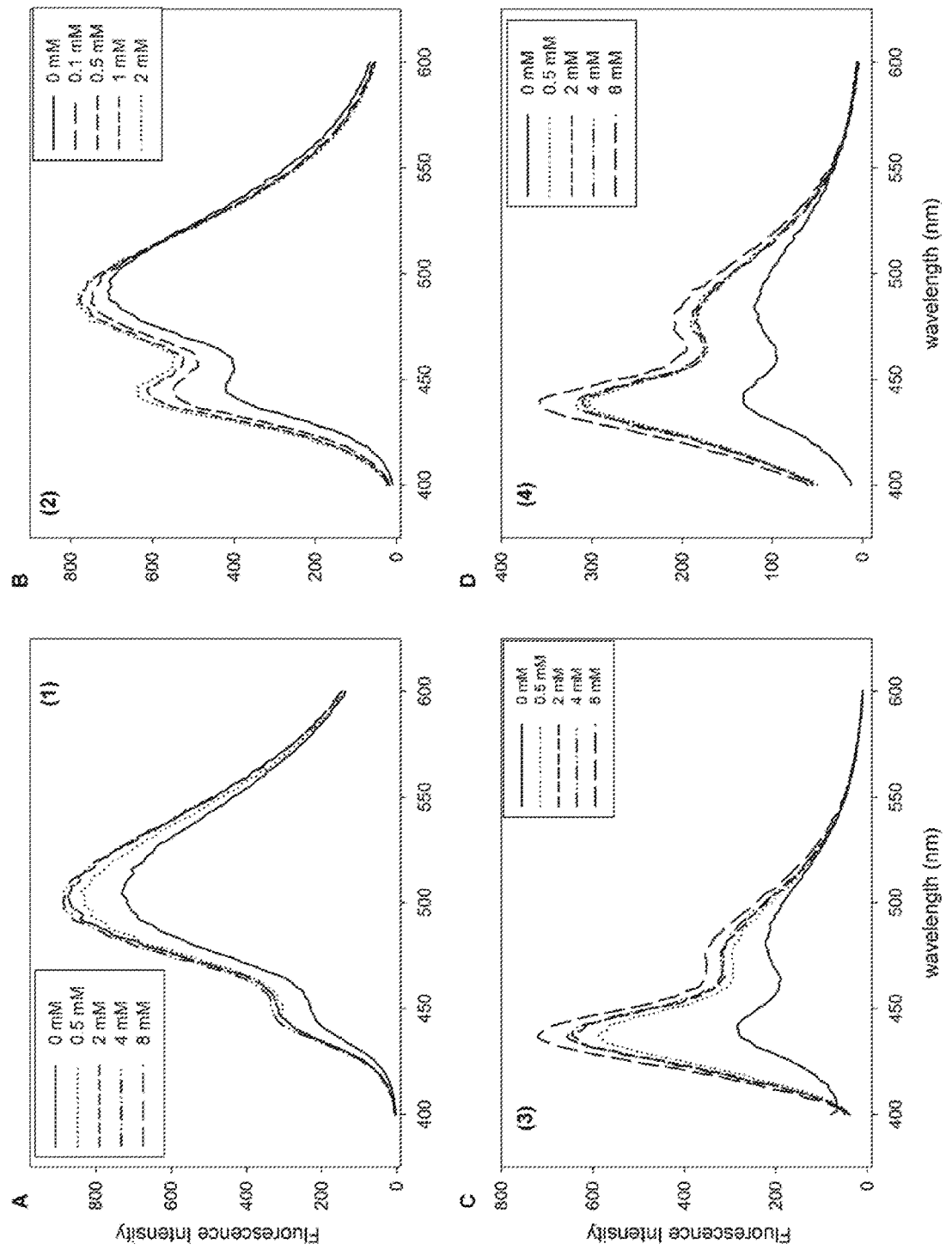
FIG. 4, panels A to D, show fluorescence emission spectra for exemplary boronic acid receptor compounds (1-4) (500 μM) with increasing lactulose 0-8 mM in 0.1 M sodium phosphate buffer pH 7.4. Excitation wavelengths used $\lambda_{wx}$=340, 330, 340, and 310 nm respectively for each receptor compound.

With reference to FIG. 4, panels A to D, the effect of lactulose on the fluorescent properties of each receptor compound (1-4) was examined in phosphate buffer pH 7.4.

Figure 2:
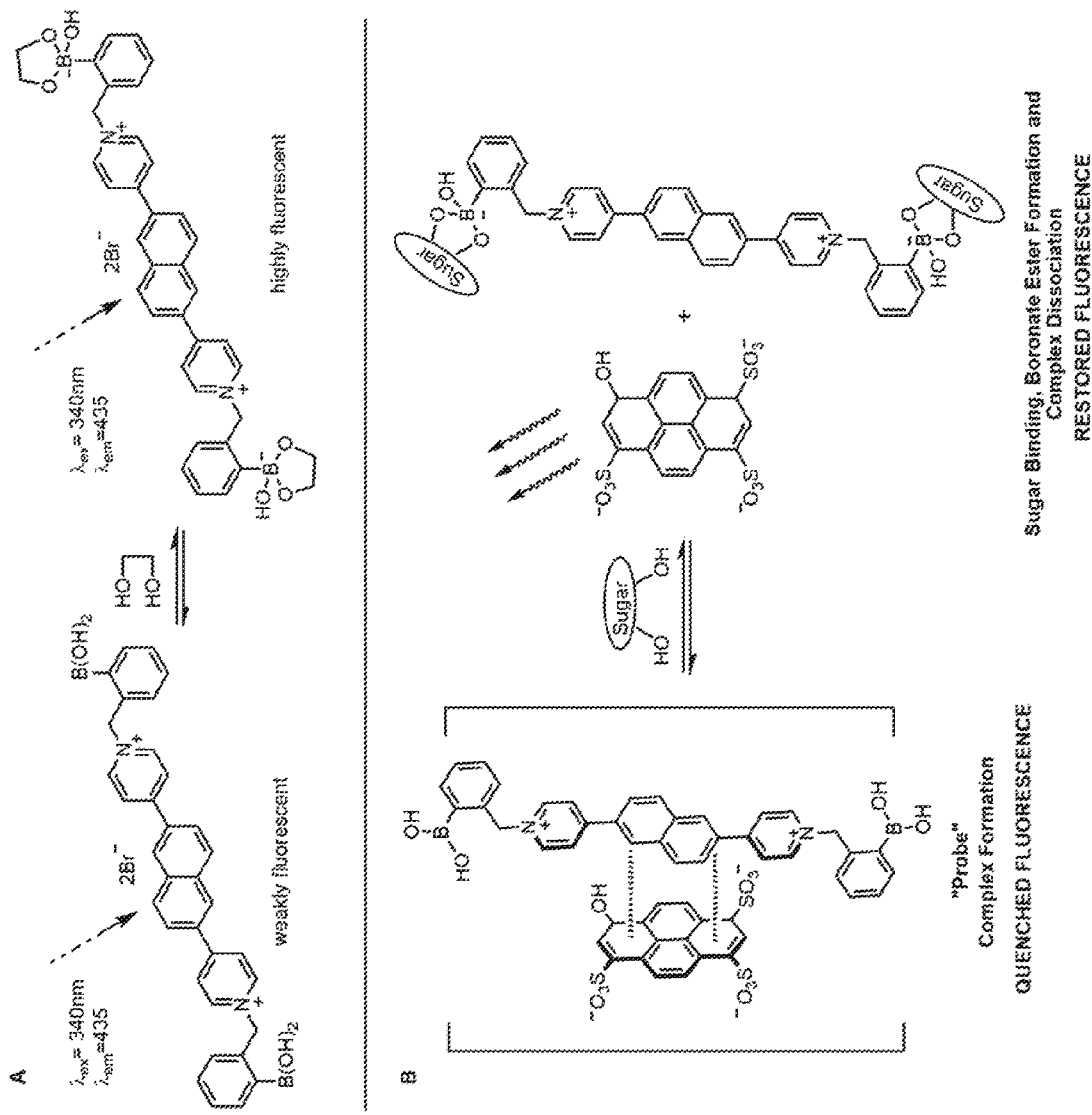
FIG. 2, panel A, illustrates the proposed formation of a fluorescent species upon diol recognition.

Receptor compounds (1) and (2) observed similar emission profiles with emission maxima at 504 and 490 nm, meanwhile the emission maxima for (3) and (4) was 50 nm less which peaked at 440 nm. For these receptor compounds, at least a 2.5-fold increase in intensity was observed in the presence of lactulose in physiological conditions. Initial introduction of lactulose (0.5 mM) provided a drastic intensity change for (3) and (4) and smaller incremental changes were observed thereafter. These types of fluorescent changes have been previously observed by Norrild where a pyridinium moiety is directly conjugated to an anthracene core (Eggert, H.; Frederiksen, J.; Morin, C.; Norrild, J. C., *Journal of Organic Chemistry* 1999, 64 (11), 3846-3852). Without being bound to any particular theory, it was hypothesized that the pyridinium unit in the subject receptor compounds may act as an electron sink for the singlet electron diminishing the fluorescence intensity. Upon boronic acid-sugar recognition and subsequently conversion of the hybridization of the boron atom from $sp^2$ to anionic $sp^3$ generating a zwitterion induces an internal charge transfer (ICT)-like mechanism increasing the fluorescence intensity. These significant fluorescent changes indicate that the subject boronic acid receptor compounds may find use as fluorescent probes for various types of sugars and sugar derivatives without the need of an additional fluorophore (e.g. HPTS, as illustrated in FIG. 2, panel B).

Example 3: Quenching of Fluorophore in Two Component Systems

Stern-Volmer quenching of HPTS and TSPP anionic reporter dyes: Stock solutions of exemplary boronic acid compounds (1, 3, and 4) were initially prepared in DMS (1 mg/mL) and then diluted in 0.1 M sodium phosphate buffer pH 7.4 to obtain the desired initial 2-fold concentration. Fluorescence measurements were conducted in a 96-well plate (Corning #3694) and to each well were added 20 μL of each exemplary compound and 8 μM of HPTS or TSPP in triplicate. Initial fluorescence wells contained 20 μL of each reporter dye and 20 μL of buffer. Blank wells received 40 μL of buffer only. Measurements were performed using a Tecan infinite M1000 instrument a plate reader (gain 100, flashes 30, z-position 1.8 cm) Plates were shaken for 30 seconds (2 mm orbital amplitude) prior to reading. After blank subtraction, fluorescence intensity relative to initial total fluorescence of HPTS or TSPP ($F_o/F$) for each sample was calculated.

Figure 5:
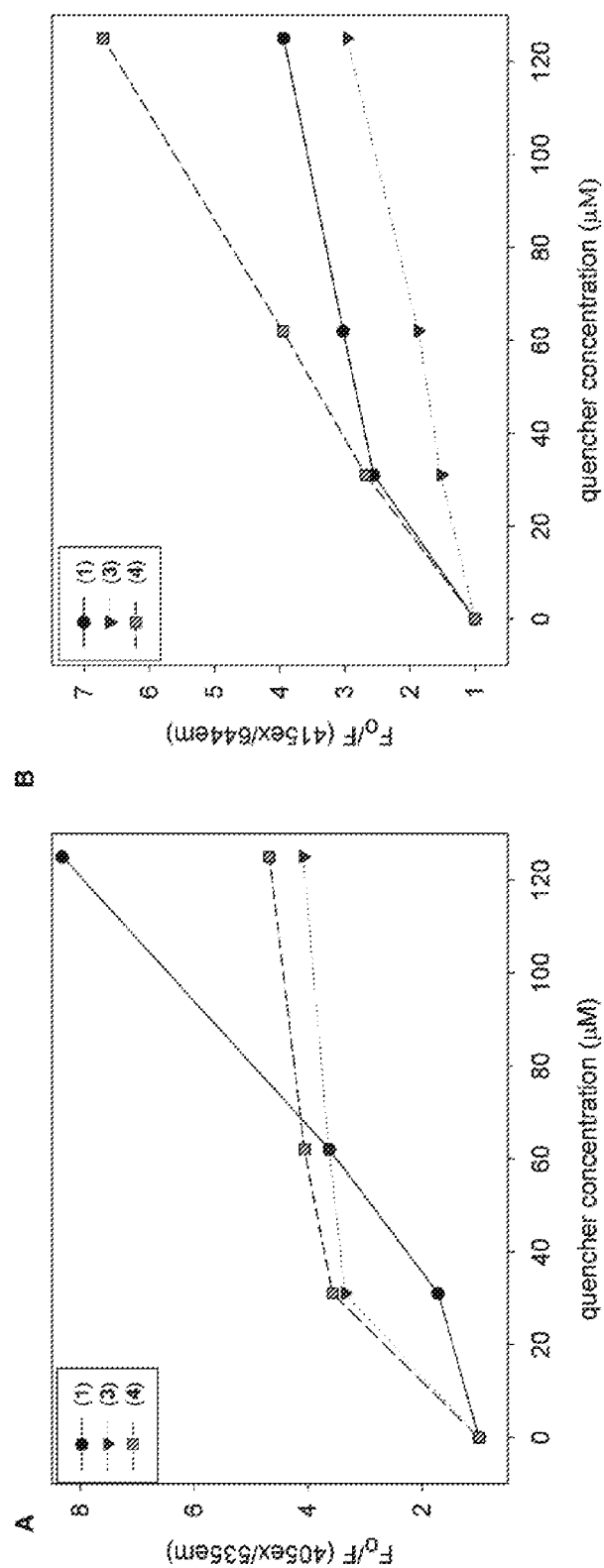
FIG. 5, panels A to B, show Stern-Volmer plot for the quenching of 4 μM HPTS (FIG. 5, panel A) or TSPP (FIG. 5, panel B) with exemplary boronic acid receptor compounds (1, 3 and 4) (0-125 μM) in 0.1 M sodium phosphate buffer pH 7.4. Excitation and emission wavelengths are provided on the axis of each graph.

Given the cationic character of the subject receptor compounds, their ability to form a non-fluorescent ground state complex with anionic reporter dyes, such as HPTS and TSPP was investigated. The fluorescence quenching of each dye can be quantitatively monitored by Stern-Volmer analysis (Albrecht, C., *Anal. Bioanal. Chem.* 2008, 390 (5), 1223-1224). Two types of quenching can exist, static quenching, due to complex formation, and dynamic quenching, due to collisional encounters between the dye and quencher. Based on previous work with bis-boronic acid appended viologens (BBV) and their ability to quench HPTS (Cordes, D. B.; Gamsey, S.; Sharrett, Z.; Miller, A.; Thoniyot, P.; Wessling, R. A.; Singaram, B., *Langmuir* 2005, 21 (14), 6540-6547), a similar quenching mechanism was envisaged for each anionic reporter dye, through static quenching. The effects of adjusting the quencher to dye ratio for HPTS and TSPP with each of compounds 1, 3, and 4 while monitoring the decrease of fluorescence for each dye are shown in FIG. 5, panel A (HPTS) and FIG. 5, panel B (TSPP).

With each of compounds 1, 3 and 4 only having two cationic groups, it was anticipated anticipated that higher (>400 μM) amounts of each quencher would be required to achieve at least 80% of quenched fluorescence. However, inventors surprisingly found, to achieve about 80% of quenched fluorescence <150 μM of each quencher (1:38) was needed. This alludes to the superior quenching ability of the exemplary compounds. It is believed that the observed superior quenching ability stems from the conjugated naphthalene core that is contributing to the π-staking when forming a ground state complex with the HPTS or TSPP fluorophore. Using the fluorescence data, the quenching efficiency can be determined using the available Stern-Volmer fitting models. The best fit to the Stern-Volmer plots for the exemplary compounds was obtained using the sphere of action quenching model (Eq. 2) (Frank, J. M.; Vavilov, S. I., *Z. Phys.* 1931, 69, 100-10).

$$\frac{F_0}{F} = (1 + K_s[Q])e^{V[Q]}$$

Where V is the dynamic quenching constant, $K_s$ is the static quenching constant, [Q] is the concentration of the quencher, and $e^{V[Q]}$ is derived from the Poisson distribution. There was higher contribution from the static quenching given the higher static quenching constants compared to the dynamic constants (Table 1).

TABLE 1

Quenching constants for exemplary quencher compounds

| Quencher/Receptor | HPTS $K_s$ (M$^{-1}$) | HPTS V(M$^{-1}$) | TSPP $K_s$ (M$^{-1}$) | TSPP V (M$^{-1}$) |
|---|---|---|---|---|
| (1) | 1.01 ± 0.5 × 10$^5$ | 63 ± 15 | 5.24 ± 0.3 × 10$^4$ | 112 ± 46 |
| (3) | 9.29 ± 0.4 × 10$^4$ | 109 ± 18 | 5.01 ± 0.7 × 10$^4$ | 68 ± 13 |
| (4) | 1.00 ± 0.9 × 10$^5$ | 100 ± 14 | 1.45 ± 0.1 × 10$^4$ | 80 ± 10 |

Due to the flexibility of the two-component system, signal modulation can be easily modified by varying the boronic acid receptor compound against the anionic fluorophore/reporter dye (HPTS or TSPP) while measuring the fluorescence recovery in the presence of an increasing sugar (e.g. lactulose). This method of determining optimal receptor-fluorophore ratio (also referred to herein as quencher-dye ratio, or Q:D ratio) can rapidly identify the limitation of each receptor compound where it is no longer responsive and determine the optimal dynamic range as illustrated in FIG. 6, panels A to F.

Figure 6:
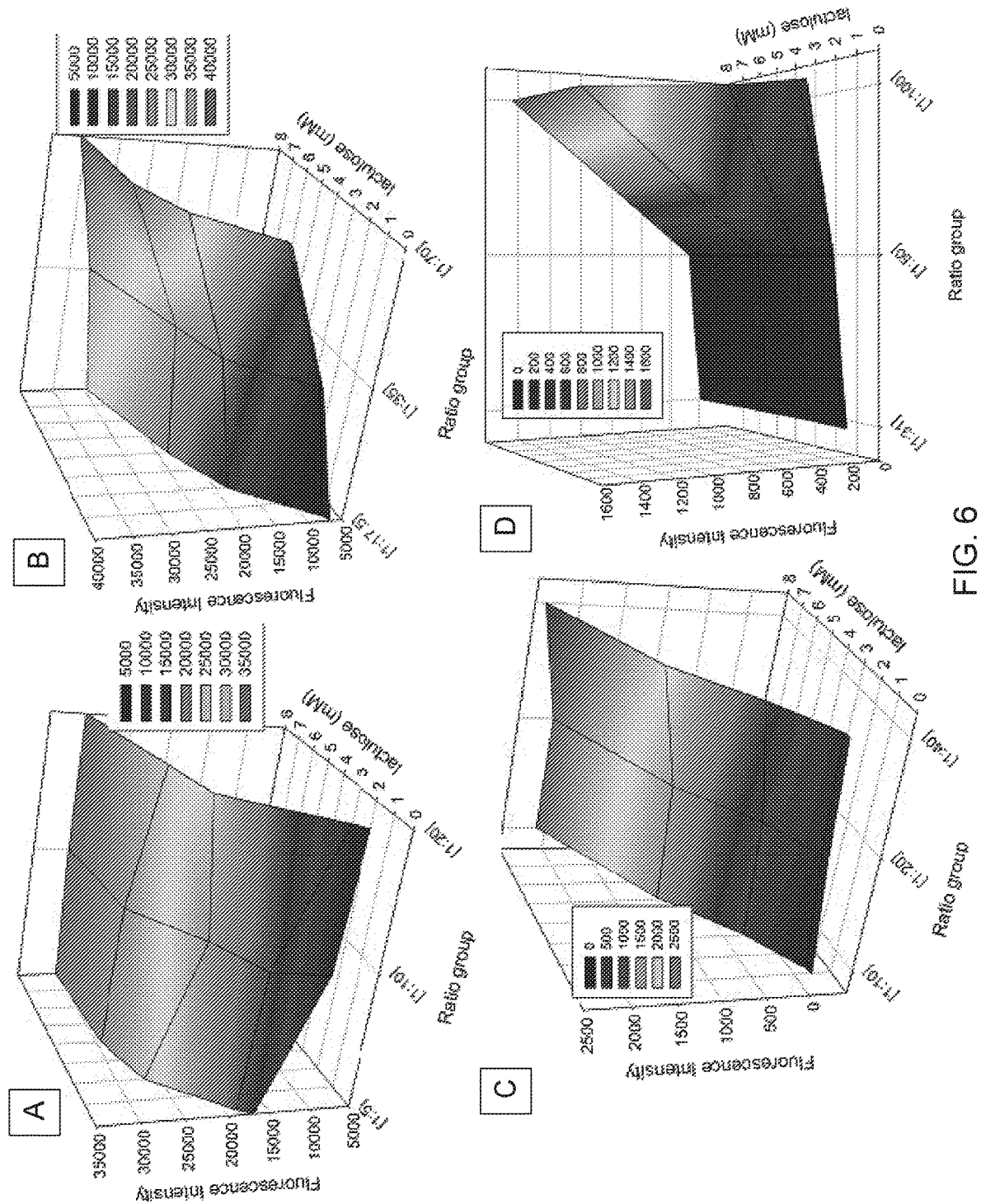
FIG. 6, illustrate varying receptor:fluorophore ratios (or quencher (Q):dye (D) ratios, Q:D ratios) for optimal signal modulation of exemplary boronic acid receptor compounds for each dye at various amounts of receptor compound to dye in the presence of increasing lactulose (0-8 mM).
Figure 6:
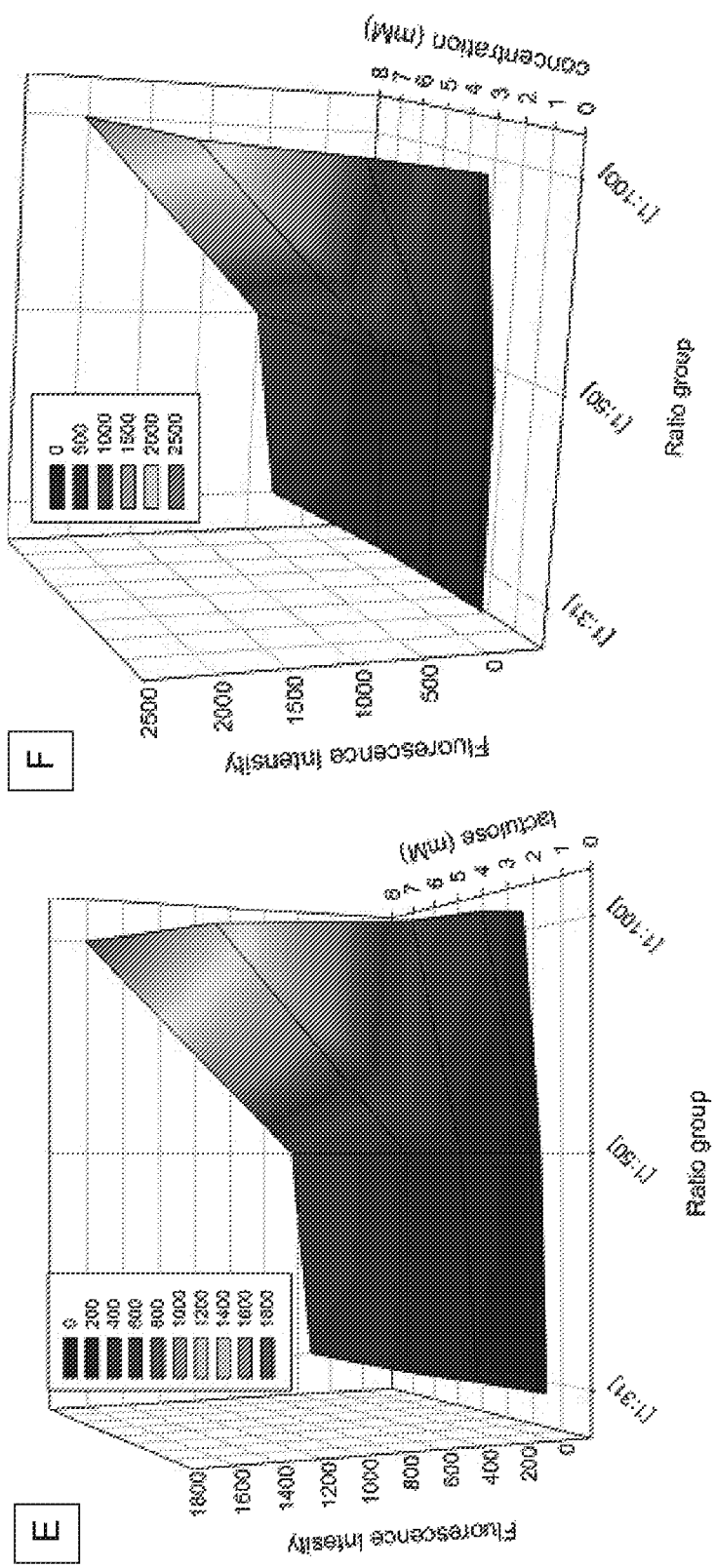

With reference to FIG. 6, panels A to F, through this simultaneous monitoring of quencher variation with increasing sugar concentrations key characteristics of each quencher-dye combination are highlighted. For the IPTS-quencher combinations, a minimal of Q:D=18:1 for (3)- and 20:1 for (1)-& (4)-HPTS to achieve the most dynamic modulation in the presence of lactulose was observed. Additionally, for the TSPP-quencher combinations, minimal Q:D of 100:1 for all three receptor compounds was observed as the optimal dynamic range. While the 100:1 for (3)-TSPP provided the highest change in fluorescence recovery, it was not a linear or hyperbolic response as usually observed with these quencher-dye combinations but instead sigmoidal. For consistency, we pursued compound combinations that provide linear or hyperbolic response and chose to use 50:1 for (3)-TSPP instead.

Example 4: Fluorescence Recovery of Fluorophore

Fluorescence recovery of each anionic reporter dyes: Fluorescence recovery measurements for sugar binding studies were conducted by preparing 96-well plates with the addition of 20 µL of the boronic acid receptor-fluorophore (HPTS or TSPP) probe solution as 2-fold concentrate (for example, 160 µM for (1) & 8 µM HPTS or 800 µM for (1) & 8 µM for TSPP) in 0.1 M sodium phosphate buffer pH 7.4. At the time of running the assay, each well received 20 µL of sample in triplicate. Blank wells were given 40 µL buffer with neither HPTS nor boronic acid receptor compound. Baseline fluorescence wells contained 20 µL of buffer and 20 µL of probe solution. Fluorescence recovery of HPTS was measured on the plate reader. After blank subtraction, fluorescence intensity relative to initial quenched HPTS ($F/F_o$) for each sample was calculated. Under these conditions, $F_o$ is a non-zero value after background subtraction with about 20% of maximum fluorescence intensity.

Figure 7:
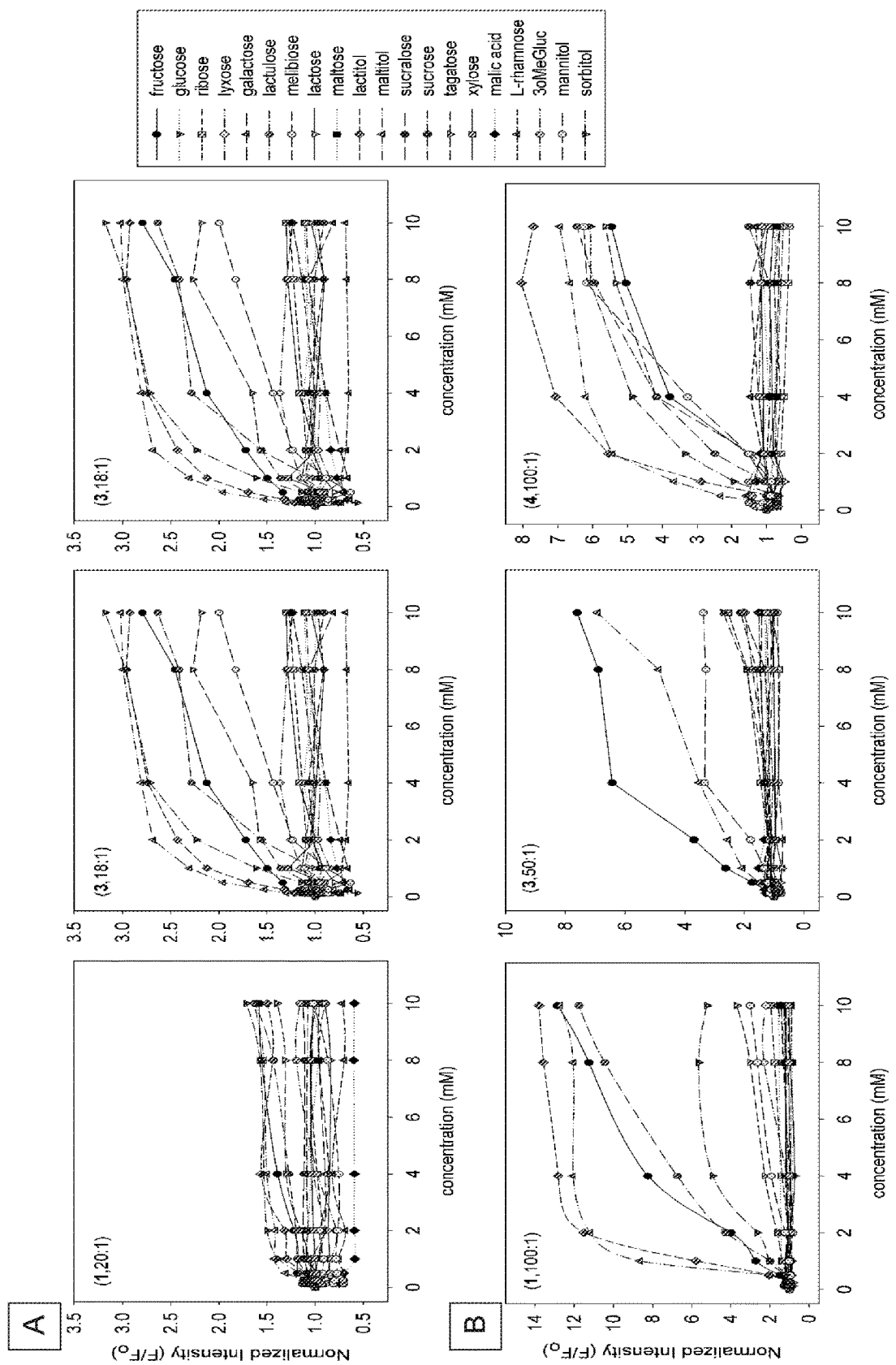
FIG. 7, panels A to B, show normalized fluorescent response for HPTS (FIG. 7, panel A) and TPPS (FIG. 7, panel B) combined with exemplary receptor compounds 1, 3 and 4 in 0.1 M sodium phosphate buffer pH 7.4. $F_o$=initial fluorescence, F:=recovered fluorescence after sugar binding. Each dye was used at 4 μM concentration and the amount of each receptor compounds is given in the parentheses of the legend.

Having established the optimal combinations between exemplary receptor compounds (1, 3 and 4) and fluorophore/anionic dye (HPTS or TSPP), the binding capabilities for a variety of sugars and sugar derivatives from aldoses to disaccharides including reducing and non-reducing sugars was investigated. The set of 20 sugars were examined with receptors (1), (3), and (4) with HPTS or TSPP anionic dye fluorophores and the corresponding optimal ratio combinations previously established see FIG. 7, panel A (HPTS) and FIG. 7, panel B (TPPS).

Each exemplary boronic acid appended naphthyl-pyridinium quencher-dye combination provided unique fluorescent recovery characteristics across all 20 sugars and sugar derivatives analyzed. For example, the (1)-HPTS combination provided minimal changes for each analyte tested, especially for those that would normally give high recovery (i.e. fructose, lactulose, sorbitol etc.), but observed only at least a 1.5-fold change in recovery. This may be attributed to the fact that there is only one boronic acid moiety and one quarternized nitrogen is neutralized. For optimal displacement of the anionic HPTS, both charges are preferably neutralized. By contrast, both (3)-HPTS and (4)-HPTS probe combinations provided good recoveries for at least seven out of the twenty sugars examined (i.e. sorbitol, lactitol, fructose, maltitol, lactulose, tagatose and mannitol).

The TSPP-receptor combinations provided significantly different binding characteristics to the HPTS-receptor combinations for the sugars examined. All combinations provided a minimum of at least a 3- to 13-fold increase in fluorescent signal. For example, (1)-TSPP gave good recoveries for lactitol, maltitol, lactulose, fructose, and sorbitol. While the (3)-TSPP probe provided selective fluorescent recovery for only fructose, maltitol, and mannitol. Lastly, the (4)-TSPP probe combination gave good fluorescent recoveries for at least seven of the twenty sugars examined similar to the (4)-HPTS probe with the exception of tagatose being preferred.

Example 5: pH Profile and Binding Characteristics

Monitoring of the pH profiles for each boronic acid receptor in the absence or presence of lactulose was carried out.

Titration curves with pH were determined using the following buffer solutions, pH 3-4 acetate buffer; pH 5-8.5 phosphate buffer; and pH 9-10 carbonate buffer. Fluorescence intensity was monitored in the absence or presence of 30 mM lactulose for exemplary receptor compounds, e.g., 2, 500 µM; 3, 250 µM; and (4, 205 M in the indicated buffer conditions. Stock solutions of each boronic acid receptor compound (2, 3, and 4) were initially prepared in DMS (1 mg/mL) and then diluted in appropriate buffer conditions to obtain the desired initial 2-fold concentration. Fluorescence measurements were conducted in a 96-well plate (Corning #3694) and to each well 30 µL of each receptor compound and buffer media with or without lactulose were added in triplicate. Blank wells received 60 µL of buffer only. Measurements were performed using a Tecan Infinite M1000 instrument, a plate reader (gain 100, flashes 30, z-position 1.8 cm) Plates were shaken for 30 seconds (2 mm orbital amplitude) prior to reading. After blank subtraction, fluorescence intensity relative to initial total fluorescence (at pH 3).

Figure 8:
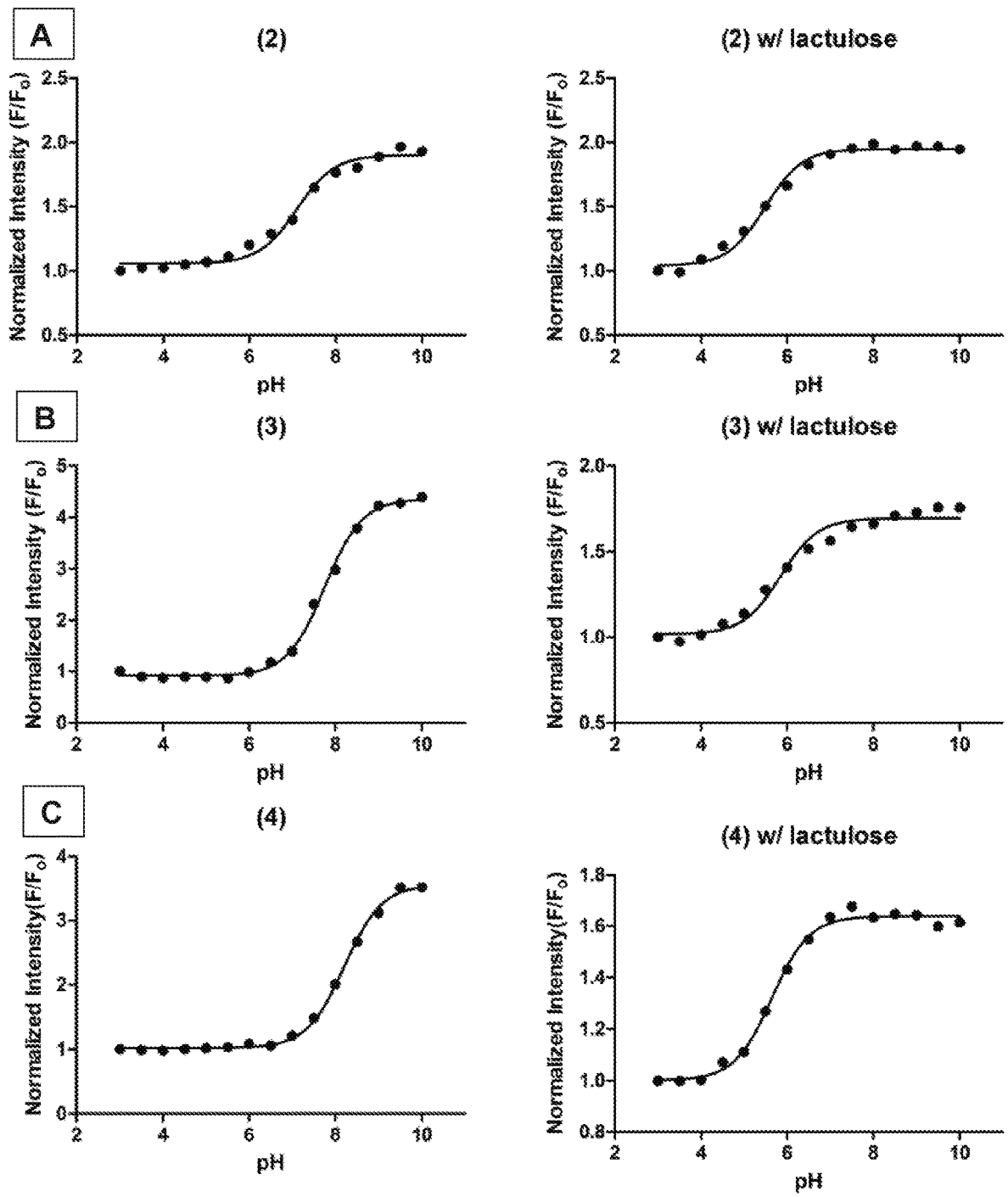
FIG. 8, panels A to C, show the pH profiles of compounds 2, 3 and 4 respectively, generated via fluorescence spectroscopy in different buffer conditions in the absence or presence of 30 mM lactulose.

FIG. 8, panels A to C, show the pH profiles of compounds 2, 3 and 4 respectively, generated via fluorescence spectroscopy in different buffer conditions in the absence or presence of 30 mM lactulose.

Each pH-profile was fitted with equation S1, where y=normalized intensity, $y_{max}$=maximum normalized intensity, $y_{min}$=minimum normalized intensity, x=pH value, k=acid dissociation constant and $pk_a$ values were obtained from this constant ($pk_a$=−log k).

$$y = \frac{y_{max} + y_{min}10^{(x-k)}}{(1 + 10^{(x-k)})} \quad \text{(Eq. S1)}$$

Table 2 shows $pK_a$ values determined by fluorescence spectroscopy of each boronic acid receptor compound in the absence or presence of lactulose in different pH conditions. Titration curves fitted to equation S1.

TABLE 2

| Boronic acid Receptor (µM) | $pk_a$-absence of lactulose | $pk_a$-with 30 mM lactulose | $R^2$ |
| --- | --- | --- | --- |
| 2 (500 µM) | 7.7 ± 0.08 | 5.5 ± 0.06 | 0.989, 0.984 |
| 3 (250 µM) | 7.8 ± 0.03 | 5.8 ± 0.10 | 0.997, 0.978 |
| 4 (250 µM) | 8.2 ± 0.02 | 5.7 ± 0.05 | 0.998, 0.994 |

Example 6: Saturation Binding Curves of Each Boronic Acid Receptor Compound

Figure 9:
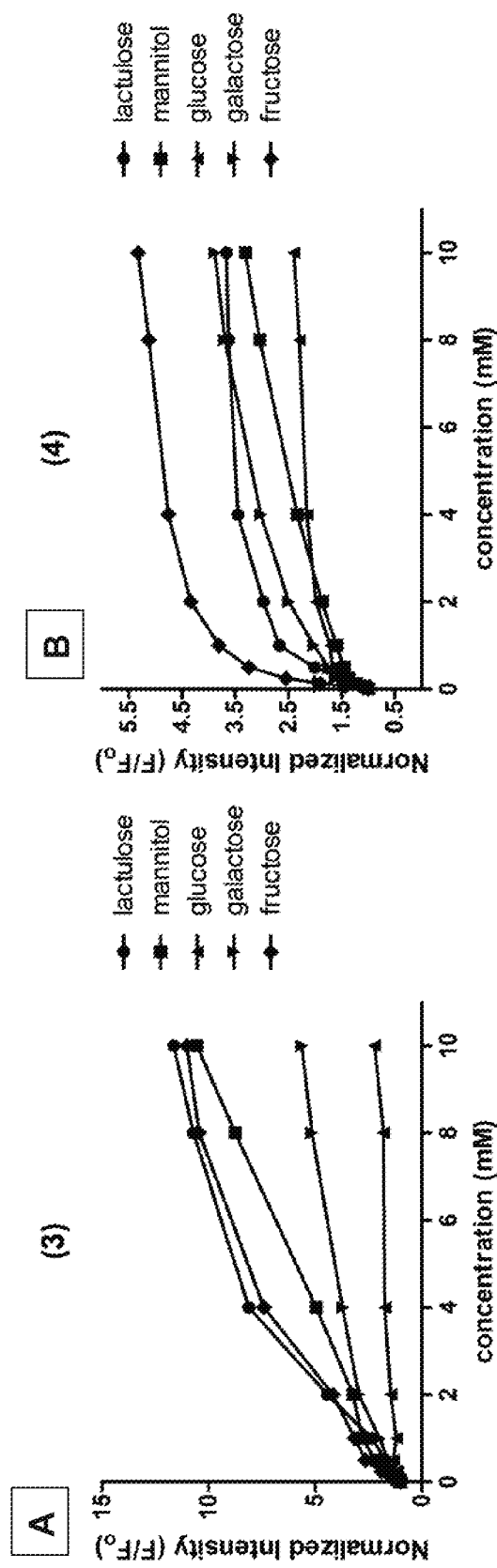
FIG. 9, panels A to B, show normalized fluorescence response of compounds 3 and 4 in the presence of lactulose, mannitol, glucose, galactose and fructose in 0.1 M sodium phosphate buffer, pH 7.4 Excitation wavelength $\lambda_{ex}$=340 nm and emission $\lambda_{em}$=435 nm was used for each receptor compound.

Fluorescence intensity was monitored with increasing sugar concentration, e.g., 0-10 mM for receptor compounds 3 (250 µM) and 4 (250 µM) in 0.1 M sodium phosphate buffer, pH 7.4. Stock solutions of each boronic acid receptor compound (3, and 4) were initially prepared in DMS (1 mg/mL) and then diluted in sodium phosphate buffer to obtain the desired initial 2-fold concentration. Fluorescence measurements were conducted in a 96-well plate (Corning #3694) and to each well 30 µL of each receptor compound and sugar in buffer media was added in triplicate. Blank wells received 60 µL of buffer only. Baseline ($F_o$) well received receptor and buffer media. Measurements were performed using a Tecan Infinite M1000 instrument, a plate reader (gain 100, flashes 30, z-position 1.8 cm) Plates were shaken for 30 seconds (2 mm orbital amplitude) prior to reading. After blank subtraction, fluorescence intensity relative to initial baseline fluorescence was plotted with respect to increasing sugar concentration (FIG. 9, panels A and B). FIG. 9, panels A and B show normalized fluorescence response of compounds 3 and 4 in the presence of lactulose, mannitol, glucose, galactose and fructose in 0.1 M sodium phosphate buffer, pH 7.4 Excitation wavelength λex=340 nm and emission λem=435 nm was used for each receptor compound.

Table 3 shows the apparent affinity constants ($K_b$, $M^{-1}$) for each boronic acid appended napthyl-pyrdinium receptor 3 and 4 for the exemplary sugars studied. The limits of detection (LOD) and quantification (LOQ) were defined as the analyte concentration in which the fluorescence intensity in the assay was 3 and 10 standard deviations above the mean baseline fluorescence.

TABLE 3

| Sugar/Boronic acid receptor | Lactulose | Mannitol | Glucose | Galactose | Fructose | LOD/LOQ (μM) |
|---|---|---|---|---|---|---|
| (3) | 1042 ± 102 | 189 ± 49 | 17 ± 3 | 473 ± 112 | 1983 ± 145 | 100/200 |
| (4) | 270 ± 30 | 13 ± 5 | 16 ± 9 | 19 ± 6 | 315 ± 20 | 70/190 |

Apparent stability constants were determined by non-linear curve fitting using equation S2.

$$\frac{F}{F_0} = \frac{\left(1 + \frac{F_{max}}{F_0}\right)K_b[A]}{1 + K_b[A]} \quad \text{Eq. S2}$$

where $F_0$ is the fluorescence intensity of the quenched dye, F is the fluorescence intensity after the addition of analyte, $F_{max}$ is the fluorescence intensity at which no further signal is obtained with further analyte addition, $K_b$ is the apparent stability constant, and [A] is analyte concentration. $K_b$ was solved using OriginLab software (Originlab Corp. Northampton, MA, USA).

Example 7: Data Analysis

Data Analysis: More generally, apparent binding constants were determined by non-linear curve fitting using the following equation (Cordes, D. B.; Gamsey, S.; Sharrett, Z.; Miller, A.; Thoniyot, P.; Wessling, R. A.; Singaram, B., Langmuir 2005, 21 (14), 6540-6547); Cooper, C. R.; James, T. D., Journal of the Chemical Society-Perkin Transactions 1 2000, (6), 963-969.

$$\frac{F}{F_0} = (F_{min} + F_{max}K[\text{sugar}])/(1 + K[\text{sugar}]) \quad (1)$$

Where $F_{min}$ is the fluorescence intensity of the quenched dye; F is the fluorescence intensity after the addition of analyte; $F_{max}$ is the fluorescence intensity at which no further signal is obtained with further analyte addition; K is the apparent binding constant and [sugar] is sugar concentration. K was solved using OriginLab software (OriginLab Corp, Northampton, MA, USA). Binding constants were calculated to compare before and after modification of aldoses.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:

1. A boronic acid receptor of formula (I):

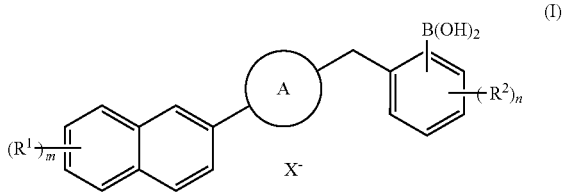

wherein:

is selected from,

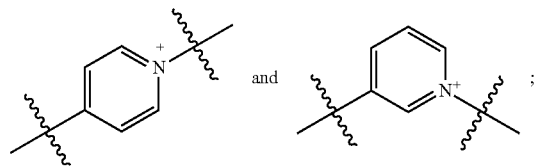

$R^1$ and $R^2$ are independently selected from an alkaryl group, a substituted alkaryl group, an aralkyl group, a substituted aralkyl group, an aryl group, a substituted aryl group, a heteroaryl group, a substituted heteroaryl group, a heteroaryl cation, a substituted heteroaryl cation, heterocycle group, a substituted heterocycle group;

n and m are independently an integer from 0 to 4; and

X is a counter ion, wherein the number of counter ions is equivalent to the number of cations in the receptor.

2. The boronic acid receptor of claim 1, wherein

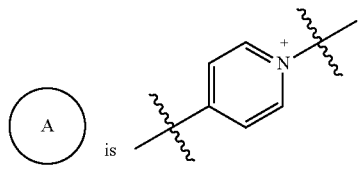

3. The boronic acid receptor of claim 1, wherein

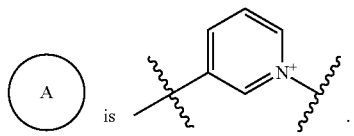

4. The boronic acid receptor according to claim 1, wherein formula (1) has the structure of formula (1A) or (IB):

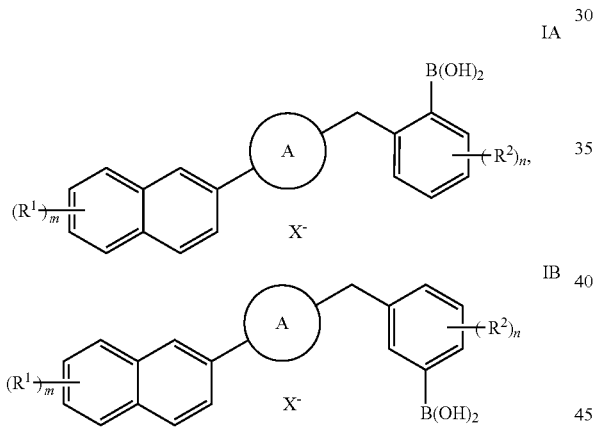

wherein:

is selected from,

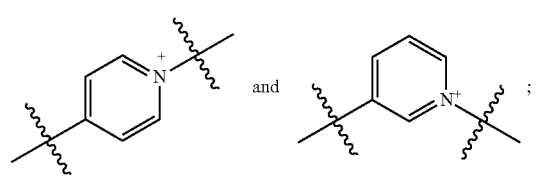

$R^1$ and $R^2$ are independently selected from an alkaryl group, a substituted alkaryl group, an aralkyl group, a substituted aralkyl group, aryl group, a substituted aryl group, a heteroaryl group, a substituted heteroaryl group, a heteroaryl cation, a substituted heteroaryl cation, heterocycle group, a substituted heterocycle group;

n and m are independently an integer from 0 to 4; and

X is a counter ion, wherein the number of counter ions is equivalent to the number of cations in the receptor.

5. The boronic acid receptor according to claim 1, wherein m is 0, n is 1 and $R^2$ is a substituted heteroaryl cation group.

6. The boronic acid receptor according to claim 1, wherein n is 0, m is 1 and $R^1$ is a substituted heteroaryl cation group.

7. The boronic acid receptor of claim 5, wherein the heteroaryl cation group is substituted with a group selected from, boronic acid, an aryl group, and an aryl substituted with a boronic acid group.

8. The boronic acid receptor according to claim 1, wherein $R^1$ and $R^2$ are independently selected from:

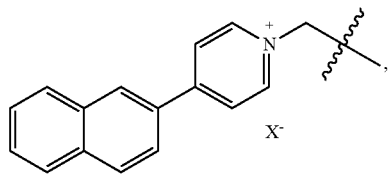

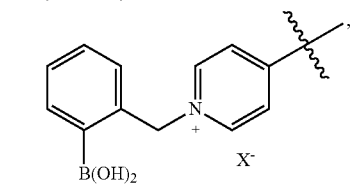

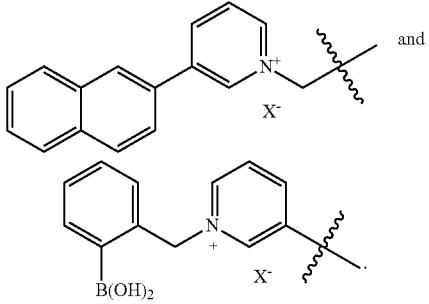

9. The boronic acid receptor according to claim 1, wherein X is a halogen.

10. The boronic acid receptor according to claim 1, wherein the number of cations and counter ions are each two.

11. The boronic acid receptor according to claim 1, wherein formula (I) is a structure selected from:

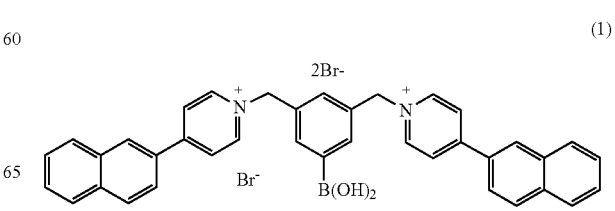

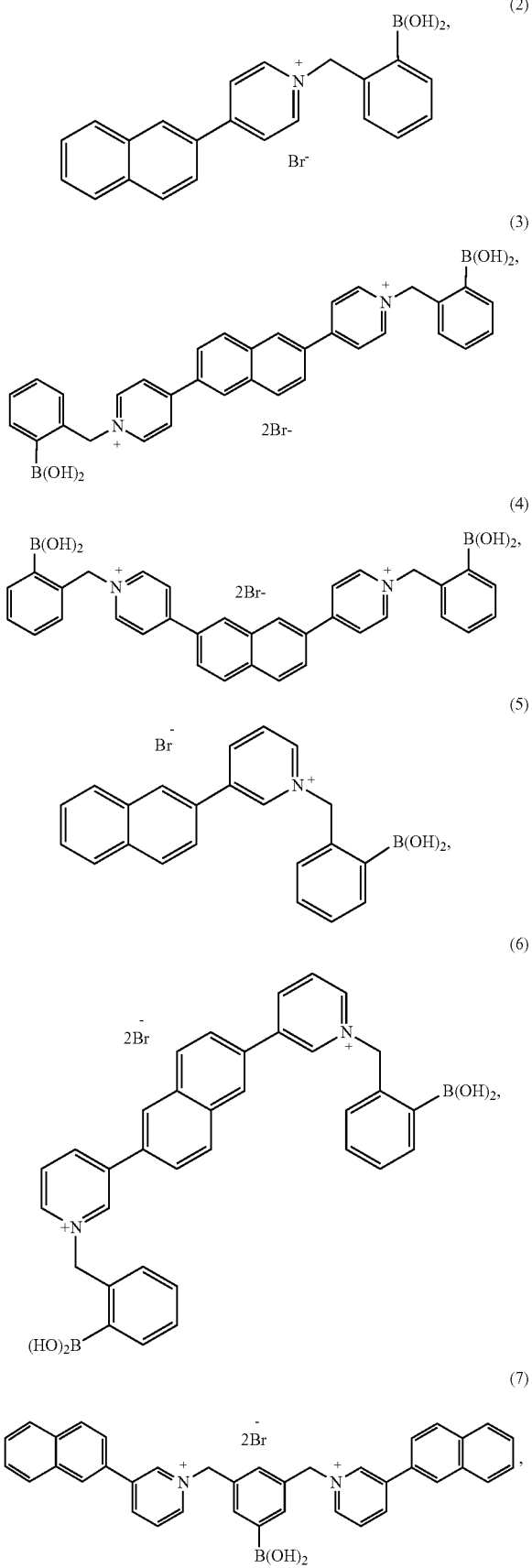
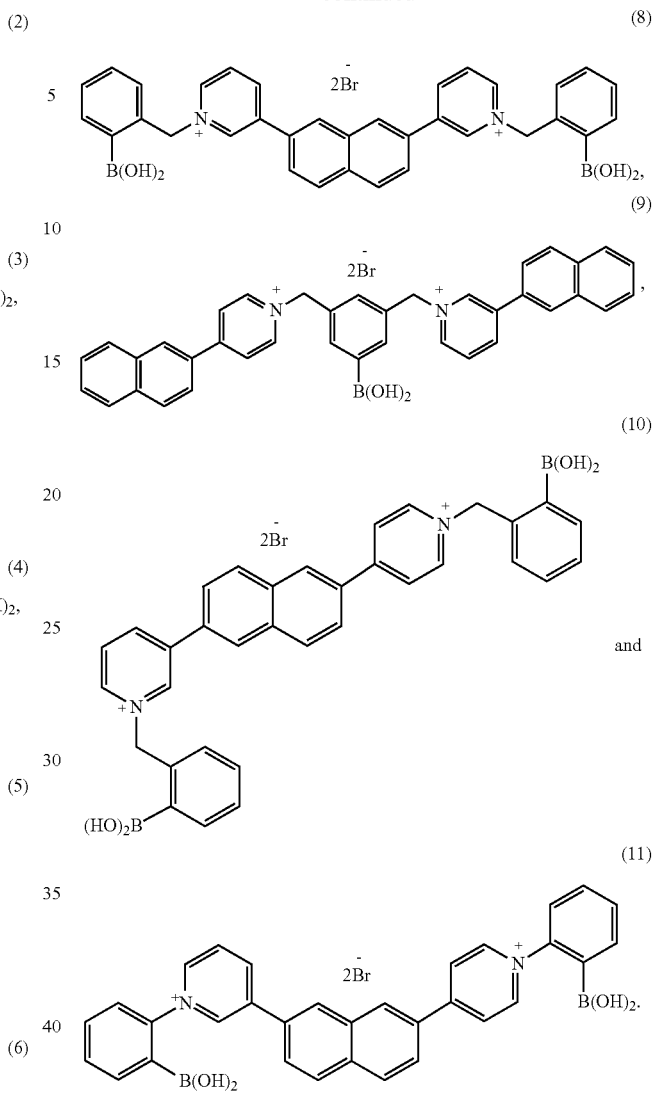

12. A method of measuring the concentration of a saccharide in a sample, the method comprising:
    contacting the sample with a boronic acid receptor according to claim 1;
    measuring the fluorescence emission of the contacted sample; and
    correlating the extent of fluorescence emission to the concentration of the saccharide in the sample.

13. The method of claim 12, wherein the boronic acid receptor is coupled to a fluorophore.

14. The method of claim 12, wherein the saccharide is a halogenated saccharide and the method first comprises:
    modifying the halogenated saccharide to generate the corresponding hydroxyl saccharide derivative.

15. The method of claim 13, wherein the fluorophore is an anionic fluorescent dye selected from 8-hydroxypyrene-1,3,6-tri sulfonic acid tri sodium salt (HPTS), or tetrakis (4-sulfophenyl) porphine (TSPP).

16. The method according to claim 12, wherein the saccharide is a non-digestible artificial sugar.

17. The method of claim 14, wherein the halogenated saccharide is sucralose, mannitol, lactulose, maltitol and lactitol, sorbitol, fructose or tagatose; or modified by a Fenton oxidation reaction, enzymatic, or photolysis approach to generate the corresponding hydroxyl saccharide derivative.

18. The method according to claim 12, wherein the sample is a biological sample obtained from an individual selected from blood or components thereof, urine, semen, sweat, saliva, tears, and fecal matter, and the method further comprises correlating the measured concentration of a saccharide in the biological sample to the gastrointestinal permeability in the individual and the individual has ingested one or more saccharides over a period of 0 to 24 hours before the biological sample is obtained, optionally ingesting riboflavin simultaneously with the one or more saccharides.

19. A fluorescence assay kit comprising a solution of a boronic acid receptor of claim 1, a buffer, and instructions for the use of the kit, wherein the solution is distributed into the wells of one or more microtiter plates.

* * * * *